US008080647B2

(12) United States Patent
Gordon-Kamm et al.

(10) Patent No.: US 8,080,647 B2
(45) Date of Patent: Dec. 20, 2011

(54) TETRACYCLINE REPRESSOR AND USES THEREOF

(75) Inventors: William J. Gordon-Kamm, Urbandale, IA (US); Keith S. Lowe, Johnston, IA (US); Christopher J. Scelonge, Ankeny, IA (US); Carl R. Simmons, Des Moines, IA (US); Aurélie Morin, Montreuil (FR); Lawrence R. Stiner, Des Moines, IA (US)

(73) Assignee: Pioneer Hi Bred International Inc, Johnston, IA (US)

( * ) Notice: Subject to any disclaimer, the term of this patent is extended or adjusted under 35 U.S.C. 154(b) by 900 days.

(21) Appl. No.: 11/940,371

(22) Filed: Nov. 15, 2007

(65) Prior Publication Data

US 2008/0201806 A1    Aug. 21, 2008

Related U.S. Application Data

(60) Provisional application No. 60/866,876, filed on Nov. 22, 2006.

(51) Int. Cl.
*C12N 15/31* (2006.01)
*C12N 15/29* (2006.01)
*A01H 5/00* (2006.01)

(52) U.S. Cl. .................. 536/23.7; 435/320.1; 435/419; 800/298; 800/306; 800/312; 800/314; 800/317.3; 800/320; 800/320.1; 800/320.2; 800/320.3; 800/322

(58) Field of Classification Search .................. None
See application file for complete search history.

(56) References Cited

U.S. PATENT DOCUMENTS

| | | | |
|---|---|---|---|
| 5,464,758 A | 11/1995 | Gossen et al. | |
| 5,589,362 A | 12/1996 | Bujard et al. | |
| 5,650,298 A | 7/1997 | Bujard et al. | |
| 5,723,765 A | 3/1998 | Oliver et al. | |
| 5,789,156 A | 8/1998 | Bujard et al. | |
| 5,814,618 A | 9/1998 | Bujard et al. | |
| 5,851,796 A | 12/1998 | Schatz | |
| 5,888,981 A | 3/1999 | Bujard et al. | |
| 6,121,014 A | 9/2000 | Koziel et al. | |
| 6,174,724 B1 | 1/2001 | Rogers et al. | |
| 6,180,774 B1 | 1/2001 | Brown et al. | |
| 6,783,756 B2 | 8/2004 | Bujard | |
| 2001/0003849 A1 | 6/2001 | Barton et al. | |
| 2003/0159184 A1* | 8/2003 | Fabijanski et al. | 800/294 |
| 2004/0148649 A1* | 7/2004 | Lydiate et al. | 800/278 |
| 2004/0224412 A1 | 11/2004 | Hannoufa et al. | |
| 2005/0034187 A1 | 2/2005 | Golovko et al. | |
| 2005/0042752 A1 | 2/2005 | Crete et al. | |
| 2005/0216976 A1 | 9/2005 | Meagher et al. | |
| 2005/0245732 A1 | 11/2005 | Hannoufa et al. | |
| 2006/0068395 A1 | 3/2006 | Wood et al. | |

FOREIGN PATENT DOCUMENTS

| | | |
|---|---|---|
| EP | 0 494 724 A2 | 7/1992 |
| WO | 9640946 | 12/1996 |
| WO | 03029453 A2 | 4/2003 |

OTHER PUBLICATIONS

Sardana et al. Construction and rapid testing of synthetic and modified toxin gene sequences CryIA (b&c) by expression in maize endosperm culture. Plant Cell Reports (1996) 15:677-681.*
Murray et al. Codon usage in plant genes. Nucleic Acids Research, vol. 17, No. 2, 1989.*
Carels et al. Compositional properties of homologous coding sequences from plants. J Mol Evol. Jan. 1998;46(1):45-53.*
Salinas et al. Compositional compartmentalization and compositional patterns in the nuclear genomes of plants. Nucleic Acids Res. May 25, 1988;16(10):4269-85.*
Gatz, et al.; "Stringent repression and homogeneous de-repression by tetracycline of a modified CaMV 35S promoter in intact transgenic tobacco plants"; The Plant Journal (1992) 2(3):397-404; Blackwell Publishing Ltd.; Oxford, UK.
Gatz, et al.; "Tn10-encoded tet repressor can regulate an operator-containing plant promoter"; Proc Natl Acad Sci USA (Mar. 1988) 85:1394-1397; National Academy of Sciences; Washington, DC, US.
Love, et al.; "Stringent control of transgene expression in *Arabidopsis thaliana* using the Top10 promoter system"; The Plant Journal (2000) 21(6):579-588; Blackwell Publishing Ltd.; Oxford, UK.
Sammarco, et al.; "A series of bidirectional tetracycline-inducible promoters provides coordinated protein expression"; Analytical Biochemistry (2005) 346:210-216; Elsevier, Inc.; The Netherlands.
Faiss, et al.; "Conditional transgenic expression of the ipt gene indicates a function for cytokinins in paracrine signalig in whole tobacco plants"; The Plant Journal (1997) 12(2):401-415; Blackwell Publishing Ltd.; Oxford, UK.
Gatz, et al.; "Regulation of a modified CaMV 35S promoter by the Tn10-encoded Tet repressor in transgenic tobacco"; Mol Gen Genet (1991) 227:229-237; Springer; Berlin/Heidelberg, Germany.
Pfam entry TetR_C; Accession No. PF02909; Tetracyclin repressor, C-terminal all-alpha domain, Oct. 17, 2006.
Pfam entry TetR_N; Accession No. PF00440; Bacterial regulatory proteins, tetR family, Oct. 17, 2006.
Weinmann, et al.; "A chimeric transactivator allows tetracycline-repsonsive gene expression in whole plants"; The Plant Journal (1994) 5(4):559-569; Blackwell Publishing Ltd.; Oxford, UK.
Thompson, et al.; "Tetracycline-dependent activation of an upstream promoter reveals transcriptional interference between tandem genes within T-DNA in tomato"; Plant Molecular Biology (1997) 34:687-692; Springer, The Netherlands.
Frohberg, et al.; "Characterization of the interaction of plant transcription factors using a bacterial repressor protein"; Proc Natl Acad Sci USA (Dec. 1991) 88:10470-10474; National Academy of Sciences; Washington, DC, US.

(Continued)

*Primary Examiner* — Cynthia Collins

(57) ABSTRACT

Compositions and methods relating to the use of tetracycline repressor in plants are provided. Compositions include a polynucleotide modified for expression in a plant, wherein the polynucleotide encodes a tetracycline repressor protein, as well as constructs, vectors, cells, plants and seeds comprising the polynucleotide, an/or produced by the methods. Also provided are methods to provide tetracycline repressor to a cell, and to regulate expression of a polynucleotide of interest in a cell, including a plant cell.

15 Claims, 2 Drawing Sheets

OTHER PUBLICATIONS

Gatz; "Chemical Control of Gene Expression"; Annu Rev Plant Physiol Plant Mol Biol (1997) 48:89-108; Annual Reviews Inc.

Padidam; "Chemically regulated gene expression in plants"; Current Opinion in Plant Biology (2003) 6:169-177; Elsevier Science Limited, Amsterdam, The Netherlands.

Corlett, et al.; "Toxicity symptoms caused by high expression of Tet repressor in tomato (*Lycopersicon esculentum* Mill. L.) are alleviated by tetracycline"; Plant, Cell and Environment (1996) 19:447-454; Blackwell Science Ltd; Oxford, UK.

Wissmann, et al.; "Tn10 tet operator mutations affecting Tet repressor recognition"; Nucleic Acids Research (1986) 14(10):4253-4266; Oxford University Press; Oxford, UK.

Scholz, et al.; "Activity reversal of Tet repressor caused by single amino acid exchanges" Molecular Microbiology (2004) 53(3):777-789; Blackwell Publishing Ltd; Oxford, UK.

Gatz, et al.; "Promoters that respond to chemical inducers"; Trends in Plant Science (Sep. 1998) 3(9):352-358; Elsevier Science Ltd; Oxford, UK.

David, et al.; "Characterization of a Tobacco Bright Yellow 2 Cell Line Expressing the Tetracycline Repressor at a High Level for Strict Regulation of Transgene Expression"; Plant Physiology (Apr. 2001) 125:1548-1553; American Society of Plant Physiologists; Rockville, MD, US.

Zuo, et al.; "Chemical-inducible systems for regulated expression of plant genes"; Current Opinion in Biotechnology (2000) 11:146-151; Elsevier Science Ltd; Amsterdam, The Netherlands.

Wells, et al.; "Codon optimization, genetic insulation, and an rtTA reporter improve performance of the tetracycline switch"; Transgenic Research (1999) 8:371-381; Kluwer Academic Publishers; The Netherlands.

Shockett, et al.; "Diverse strategies for tetracycline-regulated inducible gene expression"; Proc Natl Acad Sci USA (May 1996) 93:5173-5176; National Academy of Sciences; Washington, DC, US.

Isackson, et al.; "Dominant negative mutation in the Tn10 tet repressor: Evidence for use of the conserved helix-turn-helix motif in DNA binding"; Proc Natl Acad Sci USA (Sep. 1985) 82:6226-6230; National Academy of Sciences; Washington, DC, US.

Urlinger, et al.; "Exploring the sequence space for tetracycline-dependent transcriptional activators: Novel mutation yield expanded range and sensitivity"; Proc Natl Acad Sci (Jul. 2000) 97(14):7963-7968; National Academy of Sciences; Washington, DC, US.

Orth, et al.; "Structural basis of gene regulation by the tetracycline inducible Tet repressor-operator system"; Nature Structural Biology (Mar. 2000) 7(3):215-219; Nature America Inc.

Gossen, et al.; "Tight control of gene expression in mammalian cells by tetracycline-responsive promoters"; Proc natl Acad Sci USA (Jun. 1992) 89:5547-5551; National Academy of Sciences; Washington, DC, US.

Chrast-Balz, et al.; "Bi-directional gene switching with the tetracycline repressor and a novel tetracycline antagonist"; Nucleic Acids Research (1996) 24(15):2900-2904; Oxford University Press, Oxford, UK.

Ulmasov, et al., "Regulated expression of plant tRNA genes by the prokaryotic tet and lac repressors"; Plant Molecular Biology (1997) 35:417-424; Kluwer Academic Publishers; Belgium.

Kisker, et al.; "The Complex Formed Between Tet Repressor and Tetracycline-Mg2+ Reveals Mechanism of Antibiotic Resistance"; J Mol Biol (1995) 247:260-280; Elsevier Ltd.; Amsterdam, The Netherlands.

Gatz, "Use of the Tn10-encoded Tetracycline Repressor to Control Gene Expression"; Inducible Gene Expression; Chapter 2, pp. 11-22; CAB International, 1999.

Love, et al.; "Different Top10 promoter regulation by six tetracycline analogues in plant cells"; Journal of Experimental Botany (Sep. 2002) 53(376):1871-1877; Society for Experimental Biology; Southampton, UK.

Baron, et al.; "Tetracycline-controlled transcription in eukaryotes: novel transactovators with graded transactivation potential"; Nucleic Acids Research (1997) 25(14):2723-2729; Oxford University Press; Oxford, UK.

Tyagi, "Plant Genes and their expression"; Current Science (Jan. 2001) 80(2):161-169; Indian Academy of Science; Bangalore, India.

* cited by examiner

```
                        SEQUENCE LISTING

<160> NUMBER OF SEQ ID NOS: 16

<210> SEQ ID NO 1
<211> LENGTH: 624
<212> TYPE: DNA
<213> ORGANISM: E. coli

<400> SEQUENCE: 1
atgtctagat tagataaaag taaagtgatt aacagcgcat tagagctgct taatgaggtc        60
ggaatcgaag gtttaacaac ccgtaaactc gcccagaagc taggtgtaga gcagcctaca       120
ttgtattggc atgtaaaaaa taagcgggct ttgctcgacg ccttagccat tgagatgtta       180
gataggcacc atactcactt ttgcccttta gaaggggaaa gctggcaaga tttttttacgt      240 aataacgcta aaagttttag atgtgcttta ctaagtcatc gcgatggagc aaaagtacat       300
ttaggtacac ggcctacaga aaaacagtat gaaactctcg aaaatcaatt agcctttta       360 tgccaacaag gtttttcact agagaatgca ttatatgcac tcagcgctgt ggggcatttt       420
actttaggtt gcgtattgga agatcaagag catcaagtcg ctaaagaaga aagggaaaca       480
cctactactg atagtatgcc gccattatta cgacaagcta tcgaattatt tgatcaccaa       540
ggtgcagagc cagccttctt attcggcctt gaattgatca tatgcggatt agaaaaacaa       600
cttaaatgtg aaagtgggtc ttaa                                              624

<210> SEQ ID NO 2
<211> LENGTH: 207
<212> TYPE: PRT
<213> ORGANISM: E. coli

<400> SEQUENCE: 2

Met Ser Arg Leu Asp Lys Ser Lys Val Ile Asn Ser Ala Leu Glu Leu
  1               5                  10                  15

Leu Asn Glu Val Gly Ile Glu Gly Leu Thr Thr Arg Lys Leu Ala Gln
             20                  25                  30
```

```
Lys Leu Gly Val Glu Gln Pro Thr Leu Tyr Trp His Val Lys Asn Lys
         35                  40                  45

Arg Ala Leu Leu Asp Ala Leu Ala Ile Glu Met Leu Asp Arg His His
     50                  55                  60

Thr His Phe Cys Pro Leu Glu Gly Glu Ser Trp Gln Asp Phe Leu Arg
 65                  70                  75                  80

Asn Asn Ala Lys Ser Phe Arg Cys Ala Leu Leu Ser His Arg Asp Gly
             85                  90                  95

Ala Lys Val His Leu Gly Thr Arg Pro Thr Glu Lys Gln Tyr Glu Thr
            100                 105                 110

Leu Glu Asn Gln Leu Ala Phe Leu Cys Gln Gln Gly Phe Ser Leu Glu
            115                 120                 125

Asn Ala Leu Tyr Ala Leu Ser Ala Val Gly His Phe Thr Leu Gly Cys
        130                 135                 140

Val Leu Glu Asp Gln Glu His Gln Val Ala Lys Glu Glu Arg Glu Thr
145                 150                 155                 160

Pro Thr Thr Asp Ser Met Pro Pro Leu Leu Arg Gln Ala Ile Glu Leu
                    165                 170                 175

Phe Asp His Gln Gly Ala Glu Pro Ala Phe Leu Phe Gly Leu Glu Leu
                180                 185                 190

Ile Ile Cys Gly Leu Glu Lys Gln Leu Lys Cys Glu Ser Gly Ser
            195                 200                 205
```

<210> SEQ ID NO 3
<211> LENGTH: 624
<212> TYPE: DNA
<213> ORGANISM: Artificial Sequence
<220> FEATURE:
<223> OTHER INFORMATION: Codon modified TetRMOD1

<400> SEQUENCE: 3

```
atgtctagac tcgacaagag caaggtgatc aacagcgcac tcgagctgct gaacgaggtc      60
ggaatcgaag gcctcacaac ccgtaaactc gcccagaagc tcggtgtaga gcagcctaca     120
ttgtattggc atgtcaagaa caagcgggct tgctcgacg ccctcgccat tgagatgctc      180
gataggcacc ataccccactt ctgcccttg gaaggggaaa gctggcaaga cttcctgcgc     240
aacaacgcta gagcttcag atgtgctttg ctcagtcatc gcgatggagc caaggtccac     300
ttgggtacac ggcctacaga gaagcagtat gaaactctcg agaaccagct cgccttcctg     360
tgccaacaag gtttctccct tgagaatgcc ctctacgcac tcagcgctgt ggggcacttc     420
actctgggtt gcgtattgga agatcaagag catcaagtcg ctaaggagga gagggaaaca     480
cctactactg atagtatgcc gccactgctc cgacaagcta tcgagctctt cgatcaccaa     540
ggtgcagagc cagccttcct gttcggcctt gaattgatca tatgcggatt ggagaagcag     600
ctgaagtgtg aaagtgggtc ttaa                                            624
```

<210> SEQ ID NO 4
<211> LENGTH: 207
<212> TYPE: PRT
<213> ORGANISM: Artificial Sequence
<220> FEATURE:
<223> OTHER INFORMATION: Tetracycline repressor encoded by codon
      modified TetRMOD1

<400> SEQUENCE: 4

```
Met Ser Arg Leu Asp Lys Ser Lys Val Ile Asn Ser Ala Leu Glu Leu
  1               5                  10                  15

Leu Asn Glu Val Gly Ile Glu Gly Leu Thr Thr Arg Lys Leu Ala Gln
```

```
                20                  25                  30
Lys Leu Gly Val Glu Gln Pro Thr Leu Tyr Trp His Val Lys Asn Lys
            35                  40                  45

Arg Ala Leu Leu Asp Ala Leu Ala Ile Glu Met Leu Asp Arg His His
        50                  55                  60

Thr His Phe Cys Pro Leu Glu Gly Glu Ser Trp Gln Asp Phe Leu Arg
65                  70                  75                  80

Asn Asn Ala Lys Ser Phe Arg Cys Ala Leu Leu Ser His Arg Asp Gly
                85                  90                  95

Ala Lys Val His Leu Gly Thr Arg Pro Thr Glu Lys Gln Tyr Glu Thr
            100                 105                 110

Leu Glu Asn Gln Leu Ala Phe Leu Cys Gln Gln Gly Phe Ser Leu Glu
            115                 120                 125

Asn Ala Leu Tyr Ala Leu Ser Ala Val Gly His Phe Thr Leu Gly Cys
        130                 135                 140

Val Leu Glu Asp Gln Glu His Gln Val Ala Lys Glu Glu Arg Glu Thr
145                 150                 155                 160

Pro Thr Thr Asp Ser Met Pro Pro Leu Leu Arg Gln Ala Ile Glu Leu
                165                 170                 175

Phe Asp His Gln Gly Ala Glu Pro Ala Phe Leu Phe Gly Leu Glu Leu
            180                 185                 190

Ile Ile Cys Gly Leu Glu Lys Gln Leu Lys Cys Glu Ser Gly Ser
            195                 200                 205

<210> SEQ ID NO 5
<211> LENGTH: 624
<212> TYPE: DNA
<213> ORGANISM: Artificial Sequence
<220> FEATURE:
<223> OTHER INFORMATION: Codon modified TetRMOD3

<400> SEQUENCE: 5
atggccagac tcgacaagag caaggtgatc aacagcgcac tcgagctgct gaacgaggtc      60
ggaatcgaag gcctcacaac ccgtaaactc gcccagaagc tcggggtaga gcagcctaca     120
ttgtattggc atgtcaagaa caagcgggct ttgctcgacg ccctcgccat tgagatgctc     180
gataggcacc ataccccactt ctgccctttg aaggggaaa gctggcaaga cttcctgcgc     240
aacaacgcta agagcttcag atgtgctttg ctcagtcatc gcgatggagc caaggtccac     300
ttgggtacac ggcctacgga gaagcagtat gaaactctcg agaaccagct cgccttcctg     360
tgccaacaag gtttctccct tgagaatgcc ctctacgcac tctccgctgt ggggcacttc     420
actctgggtt gcgtattgga agatcaagag catcaagtcg ctaaggagga gagggaaaca     480
cctactactg atagtatgcc gccactgctc cgacaagcta tcgagctctt cgatcaccaa     540
ggtgcagagc cagccttcct gttcggcctt gaattgatca tatgcggatt ggagaagcag     600
ctgaagtgtg aaagtgggtc ttaa                                            624

<210> SEQ ID NO 6
<211> LENGTH: 207
<212> TYPE: PRT
<213> ORGANISM: Artificial Sequence
<220> FEATURE:
<223> OTHER INFORMATION: Tetracycline repressor encoded by codon
      modified TetRMOD3

<400> SEQUENCE: 6

Met Ala Arg Leu Asp Lys Ser Lys Val Ile Asn Ser Ala Leu Glu Leu
1               5                   10                  15
```

Leu Asn Glu Val Gly Ile Glu Gly Leu Thr Thr Arg Lys Leu Ala Gln
             20                  25                  30

Lys Leu Gly Val Glu Gln Pro Thr Leu Tyr Trp His Val Lys Asn Lys
         35                  40                  45

Arg Ala Leu Leu Asp Ala Leu Ala Ile Glu Met Leu Asp Arg His His
 50                  55                  60

Thr His Phe Cys Pro Leu Glu Gly Glu Ser Trp Gln Asp Phe Leu Arg
 65                  70                  75                  80

Asn Asn Ala Lys Ser Phe Arg Cys Ala Leu Leu Ser His Arg Asp Gly
                 85                  90                  95

Ala Lys Val His Leu Gly Thr Arg Pro Thr Glu Lys Gln Tyr Glu Thr
            100                 105                 110

Leu Glu Asn Gln Leu Ala Phe Leu Cys Gln Gln Gly Phe Ser Leu Glu
        115                 120                 125

Asn Ala Leu Tyr Ala Leu Ser Ala Val Gly His Phe Thr Leu Gly Cys
    130                 135                 140

Val Leu Glu Asp Gln Glu His Gln Val Ala Lys Glu Arg Glu Thr
145                 150                 155                 160

Pro Thr Thr Asp Ser Met Pro Pro Leu Leu Arg Gln Ala Ile Glu Leu
                165                 170                 175

Phe Asp His Gln Gly Ala Glu Pro Ala Phe Leu Phe Gly Leu Glu Leu
            180                 185                 190

Ile Ile Cys Gly Leu Glu Lys Gln Leu Lys Cys Glu Ser Gly Ser
        195                 200                 205

<210> SEQ ID NO 7
<211> LENGTH: 447
<212> TYPE: DNA
<213> ORGANISM: Artificial Sequence
<220> FEATURE:
<223> OTHER INFORMATION: 35S Triple-Op promoter

<400> SEQUENCE: 7
gaaaatcttc gtcaacatgg tggagcacga cacgcttgtc tactccaaaa atatcaaaga        60
tacagtctca gaagaccaaa gggcaattga acttttcaa caagggtaa tatccggaaa        120 cctcctcgga ttccattgcc cagctatctg tcactttatt gtgaagatag tggaaaggaa       180
aggtggctcc tacaaatgcc atcattgcga taaaggaaag gccatcgttg aagatgcctc       240
tgccgacagt ggtcccaaag atggacccc acccacgagg agcatcgtgg aaaaagaaga       300
cgttccaacc acgtcttcaa agcaagtgga ttgatgtgat atctccactg acgtaaggga       360
tgacgcacaa tcccactaga ctctatcagt gatagagtgt atataagact ctatcagtga       420
tagagtgaac tctatcagtg atagagt                                           447

<210> SEQ ID NO 8
<211> LENGTH: 33
<212> TYPE: DNA
<213> ORGANISM: Artificial Sequence
<220> FEATURE:
<223> OTHER INFORMATION: PCR primer - Forward primer PHN107613 to
      omega 5' UTR

<400> SEQUENCE: 8
tacaacaatt accaacaaca acaaacaaca aac                                     33

<210> SEQ ID NO 9
<211> LENGTH: 21
<212> TYPE: DNA

```
<213> ORGANISM: Artificial Sequence
<220> FEATURE:
<223> OTHER INFORMATION: PCR primer - reverse primer PHN107611 to ODP2

<400> SEQUENCE: 9
agaaggagat gccgccgagg a                                              21

<210> SEQ ID NO 10
<211> LENGTH: 19
<212> TYPE: DNA
<213> ORGANISM: Artificial Sequence
<220> FEATURE:
<223> OTHER INFORMATION: Tetracycline Operator used in 35S Triple-Op

<400> SEQUENCE: 10
actctatcag tgatagagt                                                 19

<210> SEQ ID NO 11
<211> LENGTH: 624
<212> TYPE: DNA
<213> ORGANISM: Artificial Sequence
<220> FEATURE:
<223> OTHER INFORMATION: Codon modified TetRMOD4

<400> SEQUENCE: 11
atggccagac tcgacaagag caaggtgatc aacagcgcac tggagctgct gaacgaggtc     60
ggaatcgaag gcctcacaac ccgtaaactc gcccagaagc tcggggtaga gcagcctaca    120
ttgtattggc acgtcaagaa caagcgggct tgctagacg ccctcgccat tgagatgctc    180
gataggcacc ataccccactt ctgcccttg gaaggggaaa gctggcaaga cttcttgagg    240
aacaacgcta agagcttcag atgtgctttg ctcagtcacc gtgatggagc caaggtccac    300
ctaggtacac ggcctacgga gaagcagtat gaaactctcg agaaccagct cgccttcctg    360
tgccaacaag gttttctccct tgagaatgcc ctctacgcac tctccgctgt agggcacttc    420
actctgggtt gcgtattgga agatcaagag caccaagtcg ctaaggagga gagggaaaca    480
cctactactg atagtatgcc gccactgctc cgacaagcta tcgagctctt cgatcaccaa    540
ggtgcagagc cagccttcct gttcggcctt gaattgatca tatgcggatt ggagaagcag    600
ctgaagtgtg aaagtgggtc ttaa                                          624

<210> SEQ ID NO 12
<211> LENGTH: 207
<212> TYPE: PRT
<213> ORGANISM: Artificial Sequence
<220> FEATURE:
<223> OTHER INFORMATION: Tetracycline repressor encoded by codon
      modified TetRMOD4

<400> SEQUENCE: 12

Met Ala Arg Leu Asp Lys Ser Lys Val Ile Asn Ser Ala Leu Glu Leu
 1               5                  10                  15

Leu Asn Glu Val Gly Ile Glu Gly Leu Thr Thr Arg Lys Leu Ala Gln
            20                  25                  30

Lys Leu Gly Val Glu Gln Pro Thr Leu Tyr Trp His Val Lys Asn Lys
        35                  40                  45

Arg Ala Leu Leu Asp Ala Leu Ala Ile Glu Met Leu Asp Arg His His
    50                  55                  60

Thr His Phe Cys Pro Leu Glu Gly Glu Ser Trp Gln Asp Phe Leu Arg
65                  70                  75                  80

Asn Asn Ala Lys Ser Phe Arg Cys Ala Leu Leu Ser His Arg Asp Gly
                85                  90                  95
```

Ala Lys Val His Leu Gly Thr Arg Pro Thr Glu Lys Gln Tyr Glu Thr
            100                 105                 110

Leu Glu Asn Gln Leu Ala Phe Leu Cys Gln Gln Gly Phe Ser Leu Glu
        115                 120                 125

Asn Ala Leu Tyr Ala Leu Ser Ala Val Gly His Phe Thr Leu Gly Cys
    130                 135                 140

Val Leu Glu Asp Gln Glu His Gln Val Ala Lys Glu Glu Arg Glu Thr
145                 150                 155                 160

Pro Thr Thr Asp Ser Met Pro Pro Leu Leu Arg Gln Ala Ile Glu Leu
                165                 170                 175

Phe Asp His Gln Gly Ala Glu Pro Ala Phe Leu Phe Gly Leu Glu Leu
            180                 185                 190

Ile Ile Cys Gly Leu Glu Lys Gln Leu Lys Cys Glu Ser Gly Ser
        195                 200                 205

<210> SEQ ID NO 13
<211> LENGTH: 624
<212> TYPE: DNA
<213> ORGANISM: Artificial Sequence
<220> FEATURE:
<223> OTHER INFORMATION: Codon modified TetRMOD2

<400> SEQUENCE: 13

```
atgtctagac tcgacaagag caaggtgatc aacagcgcac tcgagctgct gaacgaggtc      60
ggaatcgaag gcctcacaac ccgtaaactc gcccagaagc tcggtgtaga gcagcctaca     120
ttgtattggc acgtcaagaa caagcgggct ttgctagacg ccctcgccat tgagatgctc     180
gataggcacc atacccactt ctgccctttg aaggggaaa  gctggcaaga cttcttgagg     240
aacaacgcta agagcttcag atgtgctttg ctcagtcatc gcgatggagc caaggtccac     300
ttgggtacac ggcctacaga gaagcagtat gaaactctcg agaaccagct cgccttcctg     360
tgccaacaag gtttctcccct tgagaatgcc ctctacgcac tcagcgctgt agggcacttc     420
actctgggtt gcgtattgga agatcaagag catcaagtcg ctaaggagga gagggaaaca     480
cctactactg atagtatgcc gccactgctc cgacaagcta tcgagctctt cgatcaccaa     540
ggtgcagagc cagccttcct gttcggcctt gaattgatca tatgcggatt ggagaagcag     600
ctgaagtgtg aaagtgggtc ttaa                                            624
```

<210> SEQ ID NO 14
<211> LENGTH: 207
<212> TYPE: PRT
<213> ORGANISM: Artificial Sequence
<220> FEATURE:
<223> OTHER INFORMATION: Tetracycline repressor encoded by codon
      modified TetRMOD2

<400> SEQUENCE: 14

Met Ser Arg Leu Asp Lys Ser Lys Val Ile Asn Ser Ala Leu Glu Leu
1               5                   10                  15

Leu Asn Glu Val Gly Ile Glu Gly Leu Thr Thr Arg Lys Leu Ala Gln
            20                  25                  30

Lys Leu Gly Val Glu Gln Pro Thr Leu Tyr Trp His Val Lys Asn Lys
        35                  40                  45

Arg Ala Leu Leu Asp Ala Leu Ala Ile Glu Met Leu Asp Arg His His
    50                  55                  60

Thr His Phe Cys Pro Leu Glu Gly Glu Ser Trp Gln Asp Phe Leu Arg
65                  70                  75                  80

```
Asn Asn Ala Lys Ser Phe Arg Cys Ala Leu Leu Ser His Arg Asp Gly
            85                  90              95

Ala Lys Val His Leu Gly Thr Arg Pro Thr Glu Lys Gln Tyr Glu Thr
                100             105             110

Leu Glu Asn Gln Leu Ala Phe Leu Cys Gln Gln Gly Phe Ser Leu Glu
        115                 120                 125

Asn Ala Leu Tyr Ala Leu Ser Ala Val Gly His Phe Thr Leu Gly Cys
        130                 135             140

Val Leu Glu Asp Gln Glu His Gln Val Ala Lys Glu Glu Arg Glu Thr
145                 150                 155                 160

Pro Thr Thr Asp Ser Met Pro Pro Leu Leu Arg Gln Ala Ile Glu Leu
                165             170                 175

Phe Asp His Gln Gly Ala Glu Pro Ala Phe Leu Phe Gly Leu Glu Leu
            180             185                 190

Ile Ile Cys Gly Leu Glu Lys Gln Leu Lys Cys Glu Ser Gly Ser
            195             200             205

<210> SEQ ID NO 15
<211> LENGTH: 19
<212> TYPE: DNA
<213> ORGANISM: E. coli
<220> FEATURE:
<221> NAME/KEY: protein_bind
<222> LOCATION: (1)...(19)
<223> OTHER INFORMATION: Tetracycline Operator O1

<400> SEQUENCE: 15
actctatcat tgatagagt                                              19

<210> SEQ ID NO 16
<211> LENGTH: 19
<212> TYPE: DNA
<213> ORGANISM: E. coli
<220> FEATURE:
<221> NAME/KEY: protein_bind
<222> LOCATION: (1)...(19)
<223> OTHER INFORMATION: Tetracycline Operator O2

<400> SEQUENCE: 16
tccctatcag tgatagaga                                              19
```

TETRACYCLINE REPRESSOR AND USES THEREOF

CROSS-REFERENCE TO RELATED APPLICATIONS

This application claims the benefit of U.S. Application Ser. No. 60/866,876 filed Nov. 22, 2006, which is herein incorporated by reference in its entirety.

FIELD OF THE INVENTION

The invention relates to the field of molecular biology, more particularly to the regulation of gene expression.

BACKGROUND

The tetracycline operon system, comprising repressor and operator elements, was originally isolated from bacteria. The operon system is tightly controlled by the presence of tetracycline, and self-regulates the level of expression of tetA and tetR genes. The product of tetA removes tetracycline from the cell. The product of tetR is the repressor protein which binds to the operator elements with a $K_d$ of about 10 pM in the absence of tetracycline, thereby blocking expression or tetA and tetR.

This system has been modified to control expression of other polynucleotides of interest, and/or for use in other organisms. Generally, two types of tetracycline inducible systems for controlling the expression of a polynucleotide of interest are used. The first system is "off" unless the ligand is present, and uses an unmodified tetracycline repressor (TetR) or a truncated reverse mutant tetracycline repressor TetOp binding domain fused to a transactivator (rtTA). The second system is "on" in the absence of ligand, and uses a mutated tetracycline repressor (revTetR) which does not bind the operator elements in the absence of ligand, or a truncated tetracycline repressor TetOp binding domain fused to a transactivator (tTA). Typically, most systems use a tetracycline repressor DNA binding domain fragment fused to a transactivator to regulate expression.

There is a need to regulate expression of sequences of interest in plants, compositions and methods to tightly regulate expression in a plant are provided.

SUMMARY

Compositions and methods relating to the use of tetracycline repressor in plants are provided. Compositions include a polynucleotide modified for expression in a plant, wherein the polynucleotide encodes a tetracycline repressor protein, as well as constructs, vectors, cells, plants and seeds comprising the polynucleotide, and/or produced by the methods. Also provided are methods to provide tetracycline repressor to a cell, and to regulate expression of a polynucleotide of interest in a cell, including a plant cell.

DETAILED DESCRIPTION

Figure 1:
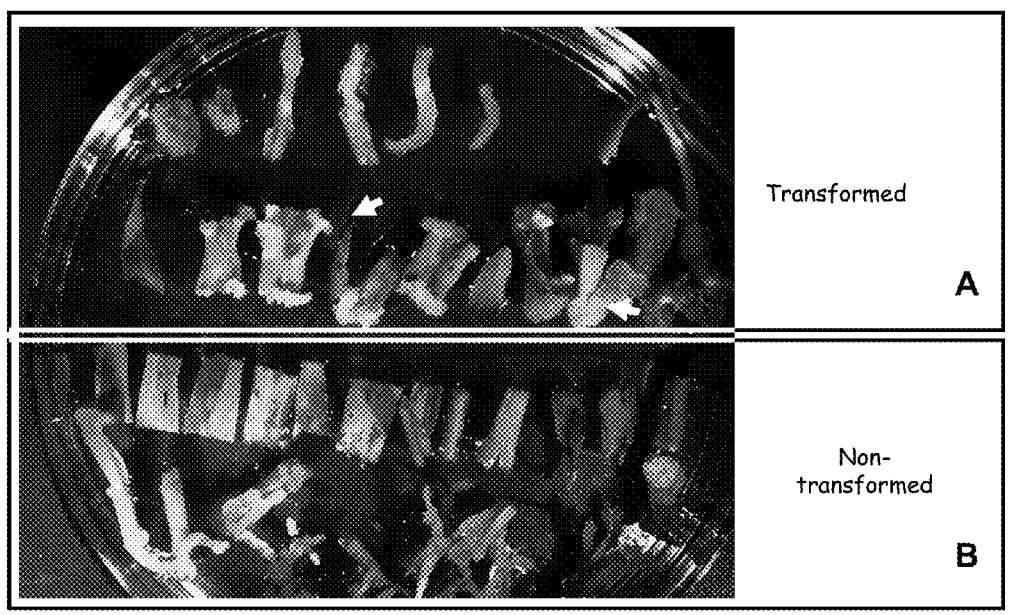
FIG. 1. Somatic embryo formation on cut edges of 1 cm segments of transgenic maize TC-inducible ODP2 T1 plantlet (A) and non-transgenic plantlet. (B) placed on culture medium containing 1 mg/L doxycycline for 2 weeks. Arrows indicate two examples of somatic embryo growth.

In the native operon context tetracycline repressor functions as a homodimer and uses two helix-turn-helix (HTH) motifs to specifically bind tandem DNA operators to block expression of the associated genes TetA and TetR. The native operators are short DNA sequences that specifically bind TetR in the absence of ligand. Operator sequences $O_1$ and $O_2$ (SEQ ID NOS: 15 and 16) from the Tn10 operon are each 19 bp with nearly identical sequence and having dyad symmetry to form two half-sites. The structure of the class D TetR protein comprises 10 alpha helices with connecting loops and turns. The 3 N-terminal helices form the DNA-binding HTH domain, which has an inverse orientation compared with HTH motifs in other DNA-binding proteins. The core of the protein, formed by helices 5-10, comprises the dimerization interface domain, and for each monomer comprises the binding pocket for ligand/effector (e.g., tetracycline) and divalent cation cofactor. Upon binding of ligand, TetR undergoes a conformational change and a reduced affinity for the operator, resulting in dissociation from the operator and derepression/induction of expression of the associated genes TetA and TetR.

Compositions and methods relating to the use of tetracycline repressor in plants are provided. Compositions include isolated polynucleotide sequences modified for expression in a plant, wherein the polynucleotide encodes a tetracycline repressor protein which binds TetOp in the absence of tetracycline or a tetracycline analog. In some examples the isolated polynucleotide is modified by substituting codons having a higher frequency of usage in a plant for codons having a lower frequency of use in a plant. In some examples the isolated polynucleotide is modified by substituting codons having a higher frequency of usage in a dicotyledonous plant for codons having a lower frequency of usage in a dicotyledonous plant. In some examples the isolated polynucleotide is modified by substituting codons having a higher frequency of usage in a monocotyledonous plant for codons having a lower frequency of usage in a monocotyledonous plant. In some examples the isolated polynucleotide is modified by substituting codons having a higher frequency of usage in a maize plant for codons having a lower frequency of usage in a maize plant.

In some examples the isolated polynucleotide comprises a modified nucleic acid sequence comprising codon substitutions as compared to a wild type tetracycline repressor, wherein the codon substitutions comprise the substitution of a codon having a higher frequency of usage in a plant for the wild type codon at that position. In some examples the isolated polynucleotide comprises a modified nucleic acid sequence comprising codon substitutions as compared to a wild type tetracycline repressor, wherein the codon substitutions comprise the substitution of a codon having a higher frequency of usage in a dicotyledonous plant for the wild type codon at that position. In some examples the isolated polynucleotide comprises a modified nucleic acid sequence comprising codon substitutions as compared to a wild type tetracycline repressor, wherein the codon substitutions comprise the substitution of a codon having a higher frequency of usage in a monocotyledonous plant for the wild type codon at that position. In some examples the isolated polynucleotide comprises a modified nucleic acid sequence comprising codon substitutions as compared to a wild type tetracycline repressor, wherein the codon substitutions comprise the substitution of a codon having the highest frequency of usage in a plant for the wild type codon at that position.

In some examples the isolated polynucleotide comprises at least 10, 15, 20, 25, 30, 35, 40, 45, 50, 55, 60, 65, 60, 75, 80, 85, 90, 95, 100 or more codon substitutions. In some examples the isolated polynucleotide comprises at least 10, 15, 20, 25, 30, 35, 40, 45, 50, 55, 60, 65, 60, 75, 80, 85, 90, 95, 100 or more codon substitutions, wherein the codon substitutions comprise the substitution of a codon having a higher frequency of usage in a plant for the wild type codon at that position. In some examples the isolated polynucleotide comprises at least 10, 15, 20, 25, 30, 35, 40, 45, 50, 55, 60, 65, 60, 75, 80, 85, 90, 95, 100 or more codon substitutions, wherein the codon substitutions comprise the substitution of a codon having a higher frequency of usage in a dicotyledonous plant for the wild type codon at that position. In some examples the isolated polynucleotide comprises at least 10, 15, 20, 25, 30, 35, 40, 45, 50, 55, 60, 65, 60, 75, 80, 85, 90, 95, 100 or more codon substitutions, wherein the codon substitutions comprise the substitution of a codon having a higher frequency of usage in a monocotyledonous plant for the wild type codon at that position. In some examples the isolated polynucleotide comprises at least 10, 15, 20, 25, 30, 35, 40, 45, 50, 55, 60, 65, 60, 75, 80, 85, 90, 95, 100 or more codon substitutions, wherein the codon substitutions comprise the substitution of a codon having a higher frequency of usage in a maize plant for the wild type codon at that position.

In some examples the isolated polynucleotide comprises at least 10, 15, 20, 25, 30, 35, 40, 45, 50, 55, 60, 65, 60, 75, 80, 85, 90, 95, 100 or more codon substitutions. In some examples the isolated polynucleotide comprising at least 10, 15, 20, 25, 30, 35, 40, 45, 50, 55, 60, 65, 60, 75, 80, 85, 90, 95, 100 or more codon substitutions has less than about 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% sequence identity to SEQ ID NO: 1, wherein the isolated polynucleotide encodes a TetR polypeptide which binds TetOp in the absence of tetracycline or an analogue thereof, wherein the sequence identity is determined over the full length of the coding sequence using a global alignment method. In some examples the isolated polynucleotide is SEQ ID NO: 3, 5, 11 or 13. In some examples the isolated polynucleotide comprising at least 10, 15, 20, 25, 30, 35, 40, 45, 50, 55, 60, 65, 60, 75, 80, 85, 90, 95, 100, or more codon substitutions encodes a polypeptide having at least about 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% sequence identity to SEQ ID NO: 2, wherein the isolated polynucleotide encodes a TetR polypeptide which binds TetOp in the absence of tetracycline or an analogue thereof, wherein the sequence identity is determined over the full length of the coding sequence using a global alignment method. In some examples the isolated polynucleotide encodes SEQ ID NO: 4, 6, 12 or 14.

In some examples the isolated polynucleotide comprises at least 10, 15, 20, 25, 30, 35, 40, 45, 50, 55, 60, 65, 60, 75, 80, 85, 90, 95, 100 or more codon substitutions, wherein the codon substitutions comprise the substitution of a codon having the highest frequency of usage in a plant for the wild type codon at that position. In some examples the isolated polynucleotide comprises at least 10, 15, 20, 25, 30, 35, 40, 45, 50, 55, 60, 65, 60, 75, 80, 85, 90, 95, 100 or more codon substitutions, wherein the codon substitutions comprise the substitution of a codon having the highest frequency of usage in a dicotyledonous plant for the wild type codon at that position. In some examples the isolated polynucleotide comprises at least 10, 15, 20, 25, 30, 35, 40, 45, 50, 55, 60, 65, 60, 75, 80, 85, 90, 95, 100 or more codon substitutions, wherein the codon substitutions comprise the substitution of a codon having the highest frequency of usage in a monocotyledonous plant for the wild type codon at that position. In some examples the isolated polynucleotide comprises at least 10, 15, 20, 25, 30, 35, 40, 45, 50, 55, 60, 65, 60, 75, 80, 85, 90, 95, 100 or more codon substitutions, wherein the codon substitutions comprise the substitution of a codon having the highest frequency of usage in a maize plant for the wild type codon at that position.

In some examples the isolated polynucleotide comprises at least 10, 15, 20, 25, 30, 35, 40, 45, 50, 55, 60, 65, 60, 75, 80, 85, 90, 95, 100 or more codon substitutions, wherein the substituted codons have a frequency of usage greater than or equal to about 0.1, 0.11, 0.12, 0.13, 0.14, 0.15, 0.16, 0.17, 0.18, 0.19, 0.2, 0.21, 0.22, 0.23, 0.24, 0.25, 0.26, 0.27, 0.28, 0.29, 0.3, 0.31, 0.32, 0.33, 0.34, 0.35 or higher. In some examples the isolated polynucleotide comprises at least 10, 15, 20, 25, 30, 35, 40, 45, 50, 55, 60, 65, 60, 75, 80, 85, 90, 95, 100 or more codon substitutions, wherein the substituted codons have a frequency of usage greater than or equal to about 0.1, 0.11, 0.12, 0.13, 0.14, 0.15, 0.16, 0.17, 0.18, 0.19, 0.2, 0.21, 0.22, 0.23, 0.24, 0.25, 0.26, 0.27, 0.28, 0.29, 0.3, 0.31, 0.32, 0.33, 0.34, 0.35 or higher in a plant. In some examples the isolated polynucleotide comprises at least 10, 15, 20, 25, 30, 35, 40, 45, 50, 55, 60, 65, 60, 75, 80, 85, 90, 95, 100 or more codon substitutions, wherein the substituted codons have a frequency of usage greater than or equal to about 0.1, 0.11, 0.12, 0.13, 0.14, 0.15, 0.16, 0.17, 0.18, 0.19, 0.2, 0.21, 0.22, 0.23, 0.24, 0.25, 0.26, 0.27, 0.28, 0.29, 0.3, 0.31, 0.32, 0.33, 0.34, 0.35 or higher in a dicotyledonous plant. In some examples the isolated polynucleotide comprises at least 10, 15, 20, 25, 30, 35, 40, 45, 50, 55, 60, 65, 60, 75, 80, 85, 90, 95, 100 or more codon substitutions, wherein the substituted codons have a frequency of usage greater than or equal to about 0.1, 0.11, 0.12, 0.13, 0.14, 0.15, 0.16, 0.17, 0.18, 0.19, 0.2, 0.21, 0.22, 0.23, 0.24, 0.25, 0.26, 0.27, 0.28, 0.29, 0.3, 0.31, 0.32, 0.33, 0.34, 0.35 or higher in a monocotyledonous plant. In some examples the isolated polynucleotide comprises at least 10, 15, 20, 25, 30, 35, 40, 45, 50, 55, 60, 65, 60, 75, 80, 85, 90, 95, 100 or more codon substitutions, wherein the substituted codons have a frequency of usage greater than or equal to about 0.1, 0.11, 0.12, 0.13, 0.14, 0.15, 0.16, 0.17, 0.18, 0.19, 0.2, 0.21, 0.22, 0.23, 0.24, 0.25, 0.26, 0.27, 0.28, 0.29, 0.3, 0.31, 0.32, 0.33, 0.34, 0.35 or higher in a maize plant.

In some examples the isolated polynucleotide comprises less than about 45, 40, 35, 30, 25, 20 or fewer codons, wherein the codons have a frequency of usage less than about 0.1, 0.11, 0.12, 0.13, 0.14, 0.15, 0.16, 0.17, 0.18, 0.19, 0.2, 0.21, 0.22, 0.23, 0.24 or 0.25. In some examples the isolated polynucleotide comprises less than about 45, 40, 35, 30, 25, 20 or fewer codons, wherein the codons have a frequency of usage less than about 0.1, 0.11, 0.12, 0.13, 0.14, 0.15, 0.16, 0.17, 0.18, 0.19, 0.2, 0.21, 0.22, 0.23, 0.24 or 0.25 in a plant. In some examples the isolated polynucleotide comprises less than about 45, 40, 35, 30, 25, 20 or fewer codons, wherein the codons have a frequency of usage less than about 0.1, 0.11, 0.12, 0.13, 0.14, 0.15, 0.16, 0.17, 0.18, 0.19, 0.2, 0.21, 0.22, 0.23, 0.24 or 0.25 in a dicotyledonous plant. In some examples the isolated polynucleotide comprises less than about 45, 40, 35, 30, 25, 20 or fewer codons, wherein the codons have a frequency of usage less than about 0.1, 0.11, 0.12, 0.13, 0.14, 0.15, 0.16, 0.17, 0.18, 0.19, 0.2, 0.21, 0.22, 0.23, 0.24 or 0.25 in a monocotyledonous plant. In some examples the isolated polynucleotide comprises less than about 45, 40, 35, 30, 25, 20 or fewer codons, wherein the codons have a frequency of usage less than about 0.1, 0.11, 0.12, 0.13, 0.14, 0.15, 0.16, 0.17, 0.18, 0.19, 0.2, 0.21, 0.22, 0.23, 0.24 or 0.25 in a maize plant.

In some examples the isolated polynucleotide comprises at least 78%, 79%, 80%, 81%, 82%, 83%, 84%, 85%, 86%, 87%, 88%, 89%, 90%, 91%, 92%, 93%, 94%, 95% or more of codons having a frequency of usage greater than or equal to about 0.1, 0.11, 0.12, 0.13, 0.14, 0.15, 0.16, 0.17, 0.18, 0.19, 0.2, 0.21, 0.22, 0.23, 0.24, 0.25, 0.26, 0.27, 0.28, 0.29, 0.3, 0.31, 0.32, 0.33, 0.34, 0.35, or higher. In some examples the isolated polynucleotide comprises at least 78%, 79%, 80%, 81%, 82%, 83%, 84%, 85%, 86%, 87%, 88%, 89%, 90%, 91%, 92%, 93%, 94%, 95%, or more of codons having a frequency of usage greater than or equal to 0.2 in a plant. In some examples the isolated polynucleotide comprises at least 78%, 79%, 80%, 81%, 82%, 83%, 84%, 85%, 86%, 87%, 88%, 89%, 90%, 91%, 92%, 93%, 94%, 95%, or more of codons having a frequency of usage greater than or equal to about 0.1, 0.11, 0.12, 0.13, 0.14, 0.15, 0.16, 0.17, 0.18, 0.19, 0.2, 0.21, 0.22, 0.23, 0.24, 0.25, 0.26, 0.27, 0.28, 0.29, 0.3, 0.31, 0.32, 0.33, 0.34, 0.35 or higher in a dicotyledonous plant. In some examples the isolated polynucleotide comprises at least 78%, 79%, 80%, 81%, 82%, 83%, 84%, 85%, 86%, 87%, 88%, 89%, 90%, 91%, 92%, 93%, 94%, 95% or more of codons having a frequency of usage greater than or equal to about 0.1, 0.11, 0.12, 0.13, 0.14, 0.15, 0.16, 0.17, 0.18, 0.19, 0.2, 0.21, 0.22, 0.23, 0.24, 0.25, 0.26, 0.27, 0.28, 0.29, 0.3, 0.31, 0.32, 0.33, 0.34, 0.35 or higher in a monocotyledonous plant. In some examples the isolated polynucleotide comprises at least 78%, 79%, 80%, 81%, 82%, 83%, 84%, 85%, 86%, 87%, 88%, 89%, 90%, 91%, 92%, 93%, 94%, 95% or more of codons having a frequency of usage greater than or equal to about 0.1, 0.11, 0.12, 0.13, 0.14, 0.15, 0.16, 0.17, 0.18, 0.19, 0.2, 0.21, 0.22, 0.23, 0.24, 0.25, 0.26, 0.27, 0.28, 0.29, 0.3, 0.31, 0.32, 0.33, 0.34, 0.35 or higher in a maize plant.

In some examples the isolated polynucleotide comprises at least 35%, 36%, 37%, 38%, 39%, 40%, 41%, 42%, 43%, 44%, 45%, 46%, 47%, 48%, 49%, 50%, 51%, 52%, 53%, 54%, 55%, 60%, 65%, 70%, 75%, 80%, 85% or more of codons having the highest frequency of usage in a plant. In some examples the isolated polynucleotide comprises at least 35%, 36%, 37%, 38%, 39%, 40%, 41%, 42%, 43%, 44%, 45%, 46%, 47%, 48%, 49%, 50%, 51%, 52%, 53%, 54%, 55%, 60%, 65%, 70%, 75%, 80%, 85% or more of codons having the highest frequency of usage in a dicotyledonous plant. In some examples the isolated polynucleotide comprises at least 35%, 36%, 37%, 38%, 39%, 40%, 41%, 42%, 43%, 44%, 45%, 46%, 47%, 48%, 49%, 50%, 51%, 52%, 53%, 54%, 55%, 60%, 65%, 70%, 75%, 80%, 85% or more of codons having the highest frequency of usage in a monocotyledonous plant. In some examples the isolated polynucleotide comprises at least 35%, 36%, 37%, 38%, 39%, 40%, 41%, 42%, 43%, 44%, 45%, 46%, 47%, 48%, 49%, 50%, 51%, 52%, 53%, 54%, 55%, 60%, 65%, 70%, 75%, 80%, 85% or more of codons having the highest frequency of usage in a maize plant.

In some examples the isolated polynucleotide comprises less than about 21%, 20%, 19%, 18%, 17%, 16%, 15%, 14%, 13%, 12%, 11%, 10% or less of codons having a frequency of usage less than about 0.1, 0.11, 0.12, 0.13, 0.14, 0.15, 0.16, 0.17, 0.18, 0.19, 0.2, 0.21, 0.22, 0.23, 0.24 or 0.25. In some examples the isolated polynucleotide comprises less than about 21%, 20%, 19%, 18%, 17%, 16%, 15%, 14%, 13%, 12%, 11%, 10% or less of codons having a frequency of usage less than about 0.1, 0.11, 0.12, 0.13, 0.14, 0.15, 0.16, 0.17, 0.18, 0.19, 0.2, 0.21, 0.22, 0.23, 0.24 or 0.25 in a plant. In some examples the isolated polynucleotide comprises less than about 21%, 20%, 19%, 18%, 17%, 16%, 15%, 14%, 13%, 12%, 11%, 10% or less of codons having a frequency of usage less than about 0.1, 0.11, 0.12, 0.13, 0.14, 0.15, 0.16, 0.17, 0.18, 0.19, 0.2, 0.21, 0.22, 0.23, 0.24 or 0.25 in a dicotyledonous plant. In some examples the isolated polynucleotide comprises less than about 21%, 20%, 19%, 18%, 17%, 16%, 15%, 14%, 13%, 12%, 11%, 10% or less of codons having a frequency of usage less than about 0.1, 0.11, 0.12, 0.13, 0.14, 0.15, 0.16, 0.17, 0.18, 0.19, 0.2, 0.21, 0.22, 0.23, 0.24 or 0.25 in a monocotyledonous plant. In some examples the isolated polynucleotide comprises less than about 21%, 20%, 19%, 18%, 17%, 16%, 15%, 14%, 13%, 12%, 11%, 10% or less of codons having a frequency of usage less than about 0.1, 0.11, 0.12, 0.13, 0.14, 0.15, 0.16, 0.17, 0.18, 0.19, 0.2, 0.21, 0.22, 0.23, 0.24 or 0.25 in a maize plant.

In some examples the isolated polynucleotide comprises codon substitutions, wherein at least 35%, 36%, 37%, 38%, 39%, 40%, 41%, 42%, 43%, 44%, 45%, 46%, 47%, 48%, 49%, 50%, 51%, 52%, 53%, 54%, 55%, 60%, 65%, 70%, 75%, 80%, 85%, 90%, 95% or more of the codons have been changed as compared to the wild type sequence. In some examples the isolated polynucleotide comprises codon substitutions, wherein at least 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 60%, 65%, 70%, 75%, 80%, 85%, 90%, 95% or more of the codons have been changed to a codon having a higher frequency of usage in a plant as compared to the wild type sequence. In some examples the isolated polynucleotide comprises codon substitutions, wherein at least 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 60%, 65%, 70%, 75%, 80%, 85%, 90%, 95% or more of the codons have been changed to a codon having a higher frequency of usage in a dicotyledonous plant as compared to the wild type sequence. In some examples the isolated polynucleotide comprises codon substitutions, wherein at least 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 60%, 65%, 70%, 75%, 80%, 85%, 90%, 95% or more of the codons have been changed to a codon having a higher frequency of usage in a monocotyledonous plant as compared to the wild type sequence. In some examples the isolated polynucleotide comprises codon substitutions, wherein at least 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 60%, 65%, 70%, 75%, 80%, 85%, 90%, 95% or more of the codons have been changed to a codon having a higher frequency of usage in a maize plant as compared to the wild type sequence.

In some examples the isolated polynucleotide comprises codon substitutions, wherein at least 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 60%, 65%, 70%, 75%, 80%, 85%, 90%, 95% or more of the codons have been changed to a codon having the highest frequency of usage in a plant as compared to the wild type sequence. In some examples the isolated polynucleotide comprises codon substitutions, wherein at least 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 60%, 65%, 70%, 75%, 80%, 85%, 90%, 95% or more of the codons have been changed to a codon having the highest frequency of usage in a dicotyledonous plant as compared to the wild type sequence. In some examples the isolated polynucleotide comprises codon substitutions, wherein at least 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 60%, 65%, 70%, 75%, 80%, 85%, 90%, 95% or more of the codons have been changed to a codon having the highest frequency of usage in a monocotyledonous plant as compared to the wild type sequence. In some examples the isolated polynucleotide comprises codon substitutions, wherein at least 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 60%, 65%, 70%, 75%, 80%, 85%, 90%, 95% or more of the codons have been changed to a codon having the highest frequency of usage in a maize plant as compared to the wild type sequence.

In some examples the isolated polynucleotide comprises a modified nucleic acid sequence comprising a modified percent GC-base composition as compared to a wild type tetracycline repressor polynucleotide. In some examples the percent GC-base composition of the isolated polynucleotide is increased as compared to a wild type polynucleotide encoding a tetracycline repressor. In some examples the percent GC-base composition of the isolated polynucleotide is modified to a percent GC-base composition typical of a plant polynucleotide, wherein the plant polynucleotide encodes a polypeptide. In some examples the isolated polynucleotide comprises a percent GC-base composition of at least about 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65% or greater.

In some examples the isolated polynucleotide comprises codon substitutions, wherein at least 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 60%, 65%, 70%, 75%, 80%, 85%, 90%, 95% or more of the codons have been changed to a codon having a higher GC-content as compared to the wild type codon at that position. In some examples the isolated polynucleotide comprises codon substitutions, wherein at least 35, 36, 37, 38, 39, 40, 41, 42, 43, 44, 45, 46, 47, 48, 49, 50, 51, 52, 53, 54, 55, 60, 61, 62, 63, 64, 65, 66, 67, 68, 69, 70, 71, 72, 73, 74, 75, 80, 81, 82, 83, 84, 85, 86, 87, 88, 89, 90, 95, 100, 110, 120, 130, 140, 150 or more of the codons have been changed to a codon having a higher GC-content as compared to the wild type codon at that position.

In some examples, the translation initiator sequence (Kozak sequence) of the isolated polynucleotide is modified to produce a Kozak sequence with a higher efficiency of translation initiation in a plant. In some examples, the Kozak sequence of the isolated polynucleotide is modified to produce a Kozak sequence with a higher efficiency of translation initiation in a dicotyledonous plant. In some examples, the Kozak sequence of the isolated polynucleotide is modified to produce a Kozak sequence with a higher efficiency of translation initiation in a monocotyledonous plant. In some examples, the Kozak sequence of the isolated polynucleotide is modified to produce a Kozak sequence with a higher efficiency of translation initiation in a maize plant. In some examples, modification of the Kozak sequence does not produce an amino acid substitution in the encoded tetracycline repressor protein. In some examples, modification of the Kozak sequence results in at least one amino acid substitution in the encoded tetracycline repressor protein. In some examples, modification of the Kozak sequence results substitution for serine at position 2 of the tetracycline repressor protein. In some examples, modification of the Kozak sequence results substitution of alanine for serine at position 2 of the tetracycline repressor protein.

In some examples the isolated polynucleotide sequence is modified by codon substitution to remove a predicted signal sequence. In some examples the isolated polynucleotide is modified by codon substitution to remove predicted plant intron splicing recognition sites. In some examples the removal of predicted plant intron splicing recognition sites by codon substitution does not modify the encoded amino acid sequence. In some examples the removal of predicted plant intron splicing recognition sites by codon substitution results in at least one amino acid substitution. In some examples the isolated polynucleotide is modified to disrupt predicted RNA secondary structure formation. In some examples the modification(s) to disrupt predicted RNA secondary structure formation does not modify the amino acid sequence of the encoded tetracycline repressor protein. In some examples the modification(s) to disrupt predicted RNA secondary structure formation results in at least one amino acid substitution. In some examples the isolated polynucleotide is modified to disrupt predicted RNA instability site(s). In some examples the modification(s) to disrupt predicted RNA instability site(s) does not modify the amino acid sequence of the encoded tetracycline repressor protein. In some examples the modification(s) to disrupt predicted RNA instability site(s) results in at least one amino acid substitution.

In some examples the isolated polynucleotide is modified to eliminate or disrupt predicted spurious open reading frame(s). In some examples the modification(s) to disrupt predicted spurious open reading frame(s) does not modify the amino acid sequence of the encoded tetracycline repressor protein. In some examples the modification(s) to disrupt predicted spurious open reading frame(s) results in at least one amino acid substitution. In some examples the isolated polynucleotide is modified to disrupt predicted spurious polyadenylation site(s). In some examples the modification(s) to disrupt predicted spurious polyadenylation site(s) does not modify the amino acid sequence of the encoded tetracycline repressor protein. In some examples the modification(s) to disrupt predicted spurious polyadenylation site(s) results in at least one amino acid substitution.

In some examples the isolated polynucleotide comprises at least one codon modification including but not limited to substitution with a codon having a higher frequency of usage in a plant, substitution with a codon having a higher frequency of usage in a dicotyledonous plant, substitution with a codon having a higher frequency of usage in a monocotyledonous plant, substitution with a codon having a higher GC base composition, substitution with a codon to produce a Kozak sequence with a higher efficiency of translation initiation in a plant, substitution with a codon to remove a predicted signal sequence, substitution with a codon to remove a predicted intron splicing signal sequence, substitution with a codon to disrupt a predicted RNA secondary structure, and substitution with a codon to disrupt a spurious open reading frame. In some examples the isolated polynucleotide comprises a combination of codon modifications, including but not limited to substitution with a codon having a higher frequency of usage in a plant, substitution with a codon having a higher frequency of usage in a dicotyledonous plant, substitution with a codon having a higher frequency of usage in a monocotyledonous plant, substitution with a codon having a higher GC base composition, substitution with a codon to produce a Kozak sequence with a higher efficiency of translation initiation in a plant, substitution with a codon to remove a predicted signal sequence, substitution with a codon to remove a predicted intron splicing signal sequence, substitution with a codon to disrupt a predicted RNA secondary structure, and substitution with a codon to disrupt a spurious open reading frame. In some examples the isolated polynucleotide comprises SEQ ID NOS: 3, 5, 11 or 13.

Other compositions provided include expression cassettes, DNA constructs, vectors, cells, plant cells, plant tissues, plants and seeds comprising an isolated polynucleotide comprising at least one codon or other nucleotide sequence modification, wherein the isolated polynucleotide encodes a tetracycline repressor polypeptide which binds TetOp in the absence of tetracycline or analog thereof, and cells, plant cells, plant tissues, plants and seeds produced by the methods.

Methods provided include methods to express a tetracycline repressor polypeptide in a plant cell. Methods to express a tetracycline repressor polypeptide in a plant cell comprise providing to the plant cell an isolated polynucleotide modified for expression in a plant as described herein, wherein the polynucleotide is operably linked to a promoter functional in the plant cell, and wherein the polynucleotide encodes a TetR polypeptide; and, expressing the polynucleotide produce the TetR polypeptide. In some examples the isolated polynucleotide is stably integrated in the genome of the plant cell. In some examples the isolated polynucleotide is transiently provided and expressed in the plant cell. In some examples the isolated polynucleotide is provided to the plant cell by sexually crossing a first plant comprising the plant cell to a second plant comprising the isolated polynucleotide encoding a TetR polypeptide operably linked to a promoter functional in the plant cell. In some examples the plant cell is from a monocot plant or a dicot plant. In some examples the plant cell is from corn, rice, wheat, barley, millet, rye, sorghum, oat, soybean, sunflower, safflower, tobacco, cotton, *Arabidopsis*, alfalfa and *Brassica*. In some examples the isolated polynucleotide is selected from the group consisting of SEQ ID NOS: 3, 5, 11 and 13. Any promoter can be operably linked to the isolated polynucleotide, in some examples the promoter operably linked to the isolated polynucleotide is a constitutive promoter, an inducible promoter, a tissue-preferred promoter, a developmentally-regulated promoter, a temporally-regulated promoter, or a spatially-regulated promoter. In some examples the method further comprises recovering a plant cell comprising the isolated polynucleotide stably incorporated in its genome. In some examples the method further comprises recovering a plant comprising the isolated polynucleotide stably incorporated in its genome. In some examples the method further comprises recovering a seed comprising the isolated polynucleotide stably incorporated into its genome.

Methods provided include methods to regulate expression of a polynucleotide of interest. Methods to regulate expression of a polynucleotide of interest in a cell comprise providing to the cell the polynucleotide of interest operably linked to a promoter which is induced by tetracycline or an analog thereof, wherein the promoter is functional in the cell; providing an isolated polynucleotide modified for expression in a plant as described herein, wherein the polynucleotide is operably linked to a promoter functional in the cell, and wherein the polynucleotide encodes a TetR polypeptide; and controlling the level of tetracycline or analog thereof, whereby the expression of the polynucleotide of interest is regulated. In some examples polynucleotide of interest is stably incorporated in the genome of the cell. Any promoter that is induced by tetracycline or an analog thereof can be operably linked to the polynucleotide of interest, in some examples the promoter operably linked to the polynucleotide of interest is a constitutive promoter, an inducible promoter, a tissue-preferred promoter, a developmentally-regulated promoter, a temporally-regulated promoter, or a spatially-regulated promoter. In some examples the promoter operably linked to the polynucleotide of interest comprises 1, 2, 3, 4, 5, 6, 7 or more tet operator sequences. In some examples the promoter operably linked to the polynucleotide of interest is a CaMV 35S 3XOpT (Triple-Op) promoter or a Top10 promoter. In some examples the promoter operably linked to the polynucleotide of interest is SEQ ID NO: 7. In some examples the isolated polynucleotide encoding TetR is stably integrated in the genome of the cell. In some examples the isolated polynucleotide is transiently provided and expressed in the cell. In some examples the isolated polynucleotide is provided to the cell by sexually crossing a first host comprising the cell to a second host comprising the isolated polynucleotide encoding a TetR polypeptide operably linked to a promoter functional in the cell. Any promoter can be operably linked to the isolated polynucleotide, in some examples the promoter operably linked to the isolated polynucleotide is a constitutive promoter, an inducible promoter, a tissue-preferred promoter, a developmentally-regulated promoter, a temporally-regulated promoter, or a spatially-regulated promoter. In some examples the cell is a plant cell. In some examples the plant cell is from a monocot plant or a dicot plant. In some examples the plant cell is from corn, rice, wheat, barley, millet, rye, sorghum, oat, soybean, sunflower, safflower, tobacco, cotton, *Arabidopsis*, alfalfa and *Brassica*. In some examples the isolated polynucleotide is selected from the group consisting of SEQ ID NOS: 3, 5, 11 and 13. In some examples the method further comprises recovering a plant cell comprising the polynucleotide of interest stably incorporated in its genome. In some examples the method further comprises recovering a plant comprising the polynucleotide of interest stably incorporated in its genome. In some examples the method further comprises recovering a seed comprising the polynucleotide of interest stably incorporated in its genome. In some examples the method further comprises recovering a plant cell, plant, and/or seed comprising both the polynucleotide of interest and the isolated polynucleotide encoding a TetR polypeptide stably incorporated into its genome.

The ability to reversibly turn genes on and off has great utility for the analyses of gene expression and function, particularly for those genes whose products are toxic to the cell. A well characterized control mechanism in prokaryotes involves repressor proteins binding to operator DNA to prevent transcription initiation (Wray and Reznikoff (1983) *J Bacteriol* 156:1188-1191) and repressor-regulated systems have been developed for controlling expression, both in animals (Wirtz and Clayton (1995) *Science* 268:1179-1183; Deuschle, et al., (1995) *Mol Cell Biol* 15:1097-1914; Furth, et al., (1994) *Proc Natl Acad Sci USA* 91:9032-9306; Gossen and Bujard (1992) *Proc Natl Acad Sci USA* 89:5547-5551; Gossen, et al., (1995) *Science* 268:1766-1769) and plants (Wilde, et al., (1992) *EMBO J* 11:1251-1259; Gatz, et al., (1992) *Plant J* 2:397-404; Roder, et al., (1994) *Mol Gen Genet* 243-32-38; Ulmasov, et al., (1997) *Plant Mol Biol* 35-417-424).

Two major systems have been successfully exploited for regulation of plant gene expression during the past decade: the lac (Ulmasov, et al., (1997) *Plant Mol Biol* 35-417-424; Wilde, et al., (1992) *EMBO J* 11:1251-1259) and the tet (Wilde, et al., (1992) *EMBO J* 11:1251-1259; Gatz, et al., (1992) *Plant J* 2:397-404; Roder, et al., (1994) *Mol Gen Genet* 243-32-38; Ulmasov, et al., (1997) *Plant Mol Biol* 35-417-424) operator-repressor systems. Both are repressor/operator based-systems deriving key elements from their corresponding prokaryotic operon, namely the *E. coli* lactose operon for lac, and the transposon Tn10 tetracycline operon for tet. Generally, these systems control the activity of a promoter by placing operator sequences near the transcriptional start site of a gene such that gene expression from the operon is inhibited upon the binding of the repressor protein to its cognate operator sequence. However, in the presence of an inducing agent, the binding of the repressor to its operator is inhibited, thus activating the promoter and enabling gene expression. In the lac system, isopropyl-B-D-thiogalactopyranoside (IPTG) is the commonly used inducing agent, while tetracycline, and/or doxycycline are commonly used inducing agents for the tet system.

Although the lac repressor has been extensively characterized, there are several advantages to using a tet repressor based system. For example, even though the lac repressor has a high association constant for its operator, and IPTG reduces the affinity of repressor for the operator by 300-fold (Barkley and Bourgeois (1980) *The Operon*, Miller and Reznikoff, Eds., Cold Spring Harbor Press, Cold Spring Harbor, N.Y., pp 177-220), only 30-fold repression has been reported using the lactose repressor (Ulmasov, et al., (1997) *Plant Mol Biol* 35-417-424). However, a 500-fold repression level has been documented using tet-based system (Gatz, et al., (1992) *Plant J* 2:397-404). Another advantage involves the toxicity of the inducing agent. The level of IPTG required to induce a lac repressor system is sufficiently high to be cytotoxic to cells. However, the level of tetracycline, or an analog thereof, required to induce expression in a tet-based system is significantly lower (Gossen, et al., (1994) *Curr Opin Biotech* 5:516-520).

Tetracycline is the parent compound of a widely used class of antibiotics. Many chemical analogs of tetracycline have been synthesized and studied for their antibacterial effects (Rogalski (1985) *The Tetracyclines*, Hlavka & Boothe, Eds., Springer-Verlag, Heidelberg, Germany, pp 179-326). Some of them have markedly different affinities for tet repressor (Degenkolb, et al., (1991) *Antimicrob Agents Chemother* 35:1591-1595) and are up to 100-fold more efficient inducers than tetracycline. The induction of these derivatives can be thermodynamically characterized (Lederer, et al., (1996) *Biochemistry* 35:7439-7446), their cell toxicity tested, and used for tet repressor-regulated expression in eukaryotic systems (Gossen, et al., (1995) *Science* 268:1766-1769). Tetracycline analogs continue to be developed and characterized. Several tetracycline analogs have been tested in plant cells including but not limited to anhydrotetracycline, doxycycline, minocycline, oxytetracycline, and GR33076X (Love, et al., (2002) *J Exp Bot* 53:1871-1877).

Expression of the Tn10-operon is regulated by binding of the tet repressor to its operator sequences (Beck, et al., (1982) *J Bacteriol* 150:633-642; Wray and Reznikoff (1983) *J Bacteriol* 156:1188-1191). The high specificity of tetracycline for the tet operator, the high efficiency of inducibility, the low toxicity of the inducer, as well as the ability of tetracycline to easily permeate most cells, are the basis for the application of the tet system in somatic gene regulation in eukaryotic cells such as from animals (Wirtz and Clayton (1995) *Science* 268:1179-1183; Gossen, et al., (1995) *Science* 268:1766-1769), humans (Deuschle, et al., (1995) *Mol Cell Biol* 15:1907-1914; Furth, et al., (1994) *Proc Natl Acad Sci USA* 91:9302-9306; Gossen and Bujard (1992) *Proc Natl Acad Sci USA* 89:5547-5551; Gossen, et al., (1995) *Science* 268:1766-1769), and plant cell cultures (Wilde, et al., (1992) *EMBO J* 11:1251-1259; Gatz, et al., (1992) *Plant J* 2:397-404; Roder, et al., (1994) *Mol Gen Genet* 243:32-28; Ulmasov, et al., (1997) *Plant Mol Biol* 35:417-424).

A number of variations of tetracycline operator/repressor systems have been devised. For example, a tetracycline based operator/repressor system was based on conversion of the tet repressor to an activator via fusion of the repressor to a transcriptional transactivation domain such as herpes simplex virus VP16 and the tet repressor (Gossen and Bujard (1992) *Proc Natl Acad Sci USA* 89:5547-5551). In this example, the effector, tetracycline, inactivates the transactivator and thereby inhibits transcription from a minimal promoter that functions solely upon binding of the tet repressor/VP16 fusion protein (tTA) to several tet operator sequences located approximately 70 bp upstream from the transcriptional start site. In the absence of tetracycline, the tTA protein binds to the operator sequences leading to transcriptional activation. This system has been used in plants (Weinmann, et al., (1994) *Plant J* 5:559-569), rat hearts (Fishman, et al., (1994) *J Clin Invest* 93:1864-1868), and mice (Furth, et al., (1994) *Proc Natl Acad Sci USA* 91:9302-9306). However, there were indications that the chimeric tTA fusion protein was toxic to cells at levels required for efficient gene regulation (Bohl, et al., (1996) *Nat Med* 3:299-305).

Promoters modified to be regulated by tetracycline and analogs thereof are known (Matzke, et al., (2003) *Plant Mol Biol Rep* 21:9-19; Padidam (2003) *Curr Op Plant Biol* 6:169-177; Gatz and Quail (1988) *Proc Natl Acad Sci USA* 85:1394-1397; Ulmasov, et al., (1997) *Plant Mol Biol* 35:417-424; Weinmann, et al., (1994) *Plant J* 5:559-569). One or more tet operator sequences can be added to a promoter in order to produce a tetracycline inducible promoter. In some examples up to 7 tet operators were introduced into the promoter (Weinmann, et al., (1994) *Plant J* 5:559-569; Love, et al., (2000) *Plant J* 21:579-588). A widely tested tetracycline regulated expression system for plants using the CaMV 35S promoter was developed. Three tet operators were introduced into the vicinity of the TATA box of the cauliflower mosaic virus (CaMV) 35S promoter, which reduced leaky expression observed with a previous 35S promoter version having two tet operators flanking the TATA box. When stably integrated into the genome of a tet repressor-positive plant, the activity of the promoter was reduced up to 500-fold. Addition of the tetracycline inducer led to full derepression of the promoter, and the subsequent activation of gene expression (Gatz, et al., (1992) *Plant J* 2:397-404). Although the tetracycline system using the 3XOpT 35S promoter generally functioned in tobacco and potato, applications in other plant systems have been problematic, including observations of toxicity and poor plant phenotype in tomato and *Arabidopsis* (Gatz (1997) *Ann Rev Plant Physiol Plant Mol Biol* 48:89-108; Corlett, et al., (1996) *Plant Cell Environ* 19:447-454). Later work demonstrated functionality of a different tet system in *Arabidopsis* using a tTA activator and the Top10 promoter comprising 7 TetOp sequences (Love, et al., (2000) *Plant J* 21:579-588).

Further studies using established plant tet systems in tobacco cell lines SR1 and Bright Yellow2 (BY2), and tobacco plants have shown variable effectiveness. In SR1 cells, the expression level of the β-glucuronidase (GUS) target gene was high under both the induced and uninduced conditions, such that expression was not stringently controlled by the presence of inducer (Boetti, et al., (1999) *Biotechnol Bioeng* 64:1-13). The tet system was unsuitable for overexpression of a cyclin-dependent kinase gene due to high basal expression coupled with low inducible expression in dividing tobacco cells (DeVeylder, et al., (2000) *J Exp Bot* 51:1647-1653). Similar to the requirement for TetR event screening observed in tobacco plants (Gatz, et al., (1992) *Plant Physiol* 2:397-404), high expressing tetR BY2 lines have been developed having stringent regulation of transgene expression (David, et al., (2001) *Plant Physiol* 125:1548-1553), but required initial selection of material having high TetR expression even when using the more tightly regulated 35S Triple-Op promoter. Out of 40 independent calli, only 3 showed proper regulation by ligand (Ahtc). RNA and protein quantification correlated with the regulation study, with high expression of tetR corresponding to proper regulation with and without ligand. Once a line was selected, it was retransformed with reporter construct, which again had to be characterized regarding control of expression with and without ligand, approximately 50% of reporter construct transformants showed proper regulation by ligand, but leaky expression was still observed in some events.

While many tet systems have been tested in plants, various deleterious effects have been observed in certain studies, for example reduction in root mass was observed in tomato and tobacco from exposure to 1 mg/ml tetracycline (Corlett, et al., (1996) *Plant Cell Environ* 19:447-454; Gatz (1997) *Ann Rev Plant Physiol Plant Mol Biol* 48:89-108). In tomato high TetR caused reduced shoot dry weight and leaf chlorophyll content, reduce leaf size, and altered phytosynthesis during late summer (July-September) (Corlett, et al., (1996) *Plant Cell Environ* 19:447-454). The TetR inducible system has not been established in *Arabidopsis* as TetR levels needed for control are not tolerated by the plants (Gatz (1997) *Ann Rev Plant Physiol Plant Mol Biol* 48:89-108). Issues have been observed in the tTA activation system as well, expression levels drop as plant ages (Weinmann, et al., (1994) *Plant J* 5:559-569), presumably from methylation of the tetOp promoter. Preliminary efforts to establish the rtTA system in tobacco or *Arabidopsis* did not work, while mRNA expression was detected as expected, but no protein was detectable by Western blot analyses (Gatz (1997) *Ann Rev Plant Physiol Plant Mol Biol* 48:89-108). No TetR, tTA, or rtTA controlled expression system has been reported for a monocot plant or cell line.

Tetracycline operator variants, mutations, synthetic operator sequences, operator position, and/or orientation have also been characterized (see, for example, Wissmann, et al., (1986) *Nucl Acids Res* 14:4253-4266; Wissmann, et al., (1988) *J Mol Biol* 202:397-406; Meier, et al., (1988) *EMBO J* 7:567-572; Sizemore, et al., (1990) *Nucl Acids Res* 18:2875-2880; Baumeister, et al., (1992) *J Mol Biol* 226:1257-1270; Gossen and Bujard (1992) *Proc Natl Acad Sci USA* 89:5547-5551; Helbl, et al., (1995) *J Mol Biol* 245:538-548; Ulmasov, et al., (1997) *Plant Mol Biol* 35:417-424; Helbl, et al., (1998) *J Mol Biol* 276:319-3244; Helbl and Hillen (1998) *J Mol Biol* 276:313-318).

In some cases, leaky expression from tetracycline inducible promoters has been observed during non-induced/repressed conditions, namely in the presence of the inducing agent for tet repressor/operator systems, or in the absence of the inducing agent for tet repressor/transactivator systems. Several approaches have been used to address this issue, including the use of reverse tetracycline repressor mutants, and transactivator fusions to tet repressor (tTA) or reverse tet repressor (rtTA), the number and placement of tet operator sequences, and use of enhancer sequences and/or MAR elements with the promoter driving tet repressor expression (see, e.g., US Publication Number 2005/0034187), and combinations of the above approaches.

Biological systems exhibit characteristic frequencies in the usage of particular codons to specify a given type of amino acid. Codon usage frequencies can differ greatly from species to species, a phenomenon known as codon bias. Species differences in codon bias are well documented in the form of codon usage frequency tables. The codon bias of a particular nucleic acid molecule will likely affect the efficiency with which the encoded polypeptide is expressed in a particular host cell and/or subcellular organelle. An mRNA comprising many rarely used codons may be less likely to be translated efficiently.

Bias in codon choice within genes in a single species appears to be related to the level of expression of the encoded protein. In unicellular organisms, such as *E. coli* and yeast, highly expressed genes typically use a smaller subset of codons than do weakly expressed genes although the codons preferred are distinct. For example, codon usage in 165 *E. coli* genes reveals a positive correlation between high expression and increased codon bias (Sharp and Li (1986) *Nucl Acids Res* 14:7734-7749), which was similarly observed in yeast (Bennetzen and Hall (1982) *J Biol Chem* 257:3026-3031). Replacement of the 25 most favored yeast codons with rare codons in the 5' end of the highly expressed gene PGK1 leads to a decrease in both mRNA and protein (Hoekema, et al., (1987) *Mol Cell Biol* 7:2914-2924). Codon usage in highly expressed genes correlates with the abundance of isoaccepting tRNAs in both yeast and *E. coli*. It has been proposed that the correlation of codon usage to isoacceptor tRNA abundance promotes high translation levels and high steady state levels of these proteins.

In general, genes within a taxonomic group exhibit similarities in codon choice, regardless of the function of these genes. The overall use of the genetic code by a taxonomic group can be estimated by summing codon frequencies of all its sequenced genes. Alternatively, the codon usage frequency for particular subsets of genes can be used to determine a codon usage frequency table. Any subset of genes can be used including but not limited to genes encoding structurally related proteins, genes encoding functionally related proteins, genes encoding proteins from different levels of taxonomic groups such as family, class, order, genus, species, subspecies, race, or strain, genes encoding proteins having a specific tissue and/or developmental distribution, and/or genes localized to a particular organelle. Adang, et al., (U.S. Pat. No. 5,567,600, herein incorporated by reference) evaluated and compared the frequency of usage in dicots and in monocots to determine whether these broader taxonomic groups are characterized by different patterns of synonymous codon preference. The 208 plant genes from 6 monocot species and 36 dicot species that were analyzed coded for proteins having a wide range of functions and varying levels of expression in different plant tissues. The frequency of codon usage in dicots versus monocots as determined by Adang, et al., (U.S. Pat. No. 5,567,600) is shown in Table 1. The relative use of synonymous codons differs between the monocots and the dicots. In general a primary difference between monocot and dicot patterns of codon usage is the percentage G+C content of the degenerate third base. In monocots, 16 of 18 amino acids favor G+C in this position, while dicots only favor G+C in 7 of 18 amino acids. The G ending codons for Thr, Pro, Ala, and Ser, which have C in codon position 2, are avoided in both monocots and dicots. The CG dinucleotide is strongly avoided in plants (Boudraa (1987) *Genet Sel Evol* 19:143-154) and other eukaryotes (Grantham, et al., (1985)

Bull Inst Pasteur 83:95-148), possibly related to methylation and methylation signals. In dicots, XCG is always the least favored codon. The doublet TA is also avoided in codon positions 2 and 3 in most eukaryotes, including both monocots and dicots.

TABLE 1

| AA | Codon | Dicots | Moncots |
|---|---|---|---|
| Ala | GCA | 0.25 | 0.16 |
|  | GCC | 0.27 | 0.38 |
|  | GCG | 0.06 | 0.22 |
|  | GCT | 0.42 | 0.24 |
| Arg | AGA | 0.30 | 0.09 |
|  | AGG | 0.25 | 0.26 |
|  | CGA | 0.08 | 0.04 |
|  | CGC | 0.11 | 0.36 |
|  | CGG | 0.04 | 0.13 |
|  | CGT | 0.21 | 0.12 |
| Asn | AAC | 0.55 | 0.75 |
|  | AAT | 0.45 | 0.25 |
| Asp | GAC | 0.42 | 0.73 |
|  | GAT | 0.58 | 0.27 |
| Cys | TGC | 0.56 | 0.70 |
|  | TGT | 0.44 | 0.30 |
| Gln | CAA | 0.59 | 0.54 |
|  | CAG | 0.41 | 0.46 |
| Glu | GAA | 0.49 | 0.25 |
|  | GAG | 0.51 | 0.75 |
| Gly | GGA | 0.38 | 0.17 |
|  | GGC | 0.16 | 0.43 |
|  | GGG | 0.12 | 0.21 |
|  | GGT | 0.33 | 0.18 |
| His | CAC | 0.46 | 0.67 |
|  | CAT | 0.54 | 0.33 |
| Ile | ATA | 0.18 | 0.11 |
|  | ATC | 0.37 | 0.64 |
|  | ATT | 0.45 | 0.24 |
| Leu | CTA | 0.08 | 0.10 |
|  | CTC | 0.19 | 0.31 |
|  | CTG | 0.09 | 0.28 |
|  | CTT | 0.28 | 0.15 |
|  | TTA | 0.10 | 0.03 |
|  | TTG | 0.26 | 0.14 |
| Lys | AAA | 0.39 | 0.14 |
|  | AAG | 0.61 | 0.86 |
| Met | ATG | 1.00 | 1.00 |
| Phe | TTC | 0.55 | 0.75 |
|  | TTT | 0.45 | 0.25 |
| Pro | CCA | 0.42 | 0.34 |
|  | CCC | 0.17 | 0.26 |
|  | CCG | 0.09 | 0.23 |
|  | CCT | 0.32 | 0.17 |
| Stop | TAA | 0.48 | 0.30 |
|  | TAG | 0.19 | 0.36 |
|  | TGA | 0.33 | 0.34 |
| Ser | AGC | 0.18 | 0.26 |
|  | AGT | 0.14 | 0.08 |
|  | TCA | 0.19 | 0.11 |
|  | TCC | 0.18 | 0.25 |
|  | TCG | 0.06 | 0.14 |
|  | TCT | 0.25 | 0.15 |
| Thr | ACA | 0.27 | 0.14 |
|  | ACC | 0.30 | 0.46 |
|  | ACG | 0.08 | 0.20 |
|  | ACT | 0.35 | 0.19 |
| Trp | TGG | 1.00 | 1.00 |
| Tyr | TAC | 0.57 | 0.79 |
|  | TAT | 0.43 | 0.21 |
| Val | GTA | 0.12 | 0.08 |
|  | GTC | 0.20 | 0.37 |
|  | GTG | 0.29 | 0.36 |
|  | GTT | 0.39 | 0.19 |

Discussions of plant codon usage have included the differences between codon choice in plant nuclear genes and in chloroplasts. Chloroplasts differ from higher plants in that they encode only 30 tRNA species. Since chloroplasts have restricted their tRNA genes, the use of preferred codons by chloroplast-encoded proteins appears more extreme. However, a positive correlation has been reported between the level of isoaccepting tRNA for a given amino acid and the frequency with which this codon is used in the chloroplast genome (Pfitzinger, et al., (1987) Nucl Acids Res 15:1377-1386).

Alternatively, a polynucleotide can be modified to reflect the codon usage frequency of a virus that infects a plant. Any plant viral sequence or combination of plant viral sequences can be used to generate a codon frequency table. Additionally various subsets of sequences, grouped by one or more criteria such as source organism, target plant, taxonomic group, encoded polypeptide function, or other criteria can be used. Viral sequences can be obtained from any source, for example a Genbank and/or NCBI taxonomy database. Plant viruses include viruses that infect monocotyledonous plants, viruses that infect dicotyledonous plants, viruses that infect both monocots and dicots, and/or viruses that infect only specific plant genera or species such as those that infect maize or soybean. The codon usage frequency can be based on all the sequenced polypeptides encode by the virus, or on any subset or combination of subsets of the polypeptides encoded by the viral nucleic acid molecules, for example polypeptides that are similar in function such as coat/capsid polypeptides, transcriptional polypeptides, translational machinery polypeptides, or envelope polypeptides, and the like. The codon usage frequency can be based on one plant virus or multiple plant viruses. Plant viral codon usage frequency tables have been generated (WO 2006/107954, herein incorporated by reference) an exemplary plant viral codon frequency table is shown in Table 2.

TABLE 2

|  |  | Monocot | | | Dicot | |
|---|---|---|---|---|---|---|
| AA | Codon | Monocot Virus | Maize Virus | Maize Capsid | Dicot Virus | Dicot Capsid |
| Ala | GCA | 0.31 | 0.31 | 0.38 | 0.33 | 0.24 |
|  | GCC | 0.21 | 0.3 | 0.22 | 0.21 | 0.27 |
|  | GCG | 0.14 | 0.11 | 0.14 | 0.13 | 0.15 |
|  | GCT | 0.34 | 0.28 | 0.26 | 0.33 | 0.34 |
| Arg | AGA | 0.32 | 0.27 | 0.3 | 0.34 | 0.24 |
|  | AGG | 0.17 | 0.17 | 0.18 | 0.23 | 0.22 |
|  | CGA | 0.14 | 0.12 | 0.18 | 0.11 | 0.12 |
|  | CGC | 0.14 | 0.19 | 0.16 | 0.09 | 0.10 |
|  | CGG | 0.09 | 0.12 | 0.11 | 0.08 | 0.11 |
|  | CGT | 0.16 | 0.13 | 0.07 | 0.15 | 0.21 |
| Asn | AAC | 0.42 | 0.44 | 0.53 | 0.41 | 0.44 |
|  | AAT | 0.58 | 0.56 | 0.47 | 0.59 | 0.56 |
| Asp | GAC | 0.38 | 0.41 | 0.45 | 0.37 | 0.32 |
|  | GAT | 0.62 | 0.59 | 0.55 | 0.63 | 0.68 |
| Cys | TGC | 0.44 | 0.42 | 0.53 | 0.41 | 0.25 |
|  | TGT | 0.56 | 0.58 | 0.47 | 0.59 | 0.75 |
| Gln | CAA | 0.58 | 0.5 | 0.52 | 0.61 | 0.59 |
|  | CAG | 0.42 | 0.5 | 0.48 | 0.40 | 0.41 |
| Glu | GAA | 0.60 | 0.52 | 0.44 | 0.61 | 0.61 |
|  | GAG | 0.40 | 0.48 | 0.56 | 0.39 | 0.39 |
| Gly | GGA | 0.37 | 0.36 | 0.42 | 0.35 | 0.32 |
|  | GGC | 0.20 | 0.23 | 0.18 | 0.18 | 0.2 |
|  | GGG | 0.14 | 0.17 | 0.23 | 0.18 | 0.18 |
|  | GGT | 0.28 | 0.24 | 0.18 | 0.29 | 0.3 |
| His | CAC | 0.43 | 0.45 | 0.35 | 0.43 | 0.35 |
|  | CAT | 0.57 | 0.55 | 0.65 | 0.57 | 0.65 |
| Ile | ATA | 0.30 | 0.27 | 0.24 | 0.31 | 0.39 |
|  | ATC | 0.29 | 0.3 | 0.36 | 0.28 | 0.26 |
|  | ATT | 0.41 | 0.43 | 0.40 | 0.41 | 0.35 |
| Leu | CTA | 0.13 | 0.12 | 0.12 | 0.12 | 0.10 |
|  | CTC | 0.14 | 0.22 | 0.18 | 0.14 | 0.13 |
|  | CTG | 0.13 | 0.16 | 0.25 | 0.12 | 0.12 |
|  | CTT | 0.18 | 0.19 | 0.12 | 0.19 | 0.14 |
|  | TTA | 0.21 | 0.14 | 0.10 | 0.22 | 0.28 |
|  | TTG | 0.21 | 0.18 | 0.23 | 0.21 | 0.23 |

TABLE 2-continued

| | | Monocot | | | Dicot | |
|---|---|---|---|---|---|---|
| AA | Codon | Monocot Virus | Maize Virus | Maize Capsid | Dicot Virus | Dicot Capsid |
| Lys | AAA | 0.53 | 0.49 | 0.48 | 0.54 | 0.54 |
| | AAG | 0.47 | 0.51 | 0.52 | 0.46 | 0.46 |
| Met | ATG | 1 | 1 | 1 | 1 | 1 |
| Phe | TTC | 0.46 | 0.56 | 0.57 | 0.44 | 0.44 |
| | TTT | 0.54 | 0.44 | 0.43 | 0.56 | 0.56 |
| Pro | CCA | 0.38 | 0.31 | 0.32 | 0.38 | 0.38 |
| | CCC | 0.17 | 0.20 | 0.24 | 0.18 | 0.18 |
| | CCG | 0.14 | 0.17 | 0.12 | 0.12 | 0.12 |
| | CCT | 0.31 | 0.32 | 032 | 0.31 | 0.31 |
| STOP | TAA | 0.34 | 0.33 | 0.50 | 0.46 | 0.46 |
| | TAG | 0.25 | 0.42 | 0 | 0.24 | 0.24 |
| | TGA | 0.41 | 0.24 | 0.50 | 0.30 | 0.30 |
| Ser | AGC | 0.13 | 0.12 | 0.19 | 0.14 | 0.14 |
| | AGT | 0.18 | 0.12 | 0.13 | 0.20 | 0.20 |
| | TCA | 0.24 | 0.22 | 0.21 | 0.23 | 0.23 |
| | TCC | 0.14 | 0.21 | 0.26 | 0.14 | 0.14 |
| | TCG | 0.10 | 0.10 | 0.06 | 0.08 | 0.08 |
| | TCT | 0.21 | 0.22 | 0.15 | 0.21 | 0.21 |
| Thr | ACA | 0.30 | 0.32 | 0.36 | 0.36 | 0.36 |
| | ACC | 0.20 | 0.26 | 0.27 | 0.20 | 0.20 |
| | ACG | 0.16 | 0.13 | 0.06 | 0.14 | 0.14 |
| | ACT | 0.34 | 0.29 | 0.31 | 0.31 | 0.31 |
| Trp | TGG | 1 | 1 | 1 | 1 | 1 |
| Tyr | TAC | 0.43 | 0.46 | 0.41 | 0.41 | 0.41 |
| | TAT | 0.57 | 0.54 | 0.59 | 0.59 | 0.59 |
| Val | GTA | 0.19 | 0.16 | 0.15 | 0.19 | 0.19 |
| | GTC | 0.21 | 0.25 | 0.26 | 0.21 | 0.21 |
| | GTG | 0.25 | 0.26 | 0.36 | 0.25 | 0.25 |
| | GTT | 0.36 | 0.33 | 0.23 | 0.35 | 0.35 |

When modifying a coding region, the A+T content may be modified to more closely reflect that typically found in native genes of the target host cell. For example, for genes encoding highly expressed plant proteins the A+T content is approximately 55%. When adjusting A+T content, consideration must be given to the overall level, and formation of possible signaling and/or regulatory sequences that may destabilize the RNA and/or lower expression levels, for example A+T rich regions are often found in intergenic regions and plant regulatory sequences.

GC content is another metric used to describe gene structure. Overall gene GC content can vary greatly between organisms, and within genes from the same organism. GC content and patterns may be related to chromosome organization and function, methylation pressure, presence of repetitive DNA, adaptations for gene expression, and/or codon-anticodon coadapted biases. The gene population of many organisms have a fairly uniform unimodal GC content. However other organisms, including some vertebrates and cereal plants, have a bimodal GC content distribution (Campbell and Gowri (1990) *Plant Physiol* 92:1-11; Bernardi (1995) *Ann Rev Genet* 29:445-475; Carels and Bernardi (2000) *Genetics* 154:1819-1825). Genome sequencing has provided additional data and evidence for bimodal GC distribution, for example in humans, rice, and corn (International Human Genome Sequencing Consortium (2001) *Nature* 409:860-921; Yu, et al., (2002) *Science* 296:79-91; Wong, et al., (2002) *Genome Res* 12:851-856; WO2004/003148; US Publication Number 2004/0210963).

Maize and other cereals, including rice and wheat, have distinctly bimodal GC content distributions for nuclear genes not observed in dicotyledonous plants. For example, the unimodal GC distribution in *Arabidopsis* is centered at about 44% for open reading frame sequences (ORFGC). In maize, the two modes center at about 51% (low) and 67% (high) GC content, with about two-thirds of the genes found in the lower GC mode. An evaluation of 111 maize chloroplast-encoded ORFs showed a unimodal distribution centered at about 39.1% ORFGC, and 16 mitochondrial-encoded ORFs averaged about 43.4% GC content (Simmons, et al., (2002) Maize Coop Newsletter at agron.missouri.edu/mnl website). In maize, most GC content variation is found in the third position of the codon, which can reach 100%, and in high GC mode genes, C can be favored over G by 3:1. There can also be a variation in the pattern of GC content within a coding region, for example maize genes generally have a negative GC gradient wherein GC content decreases toward the 3' end of the coding region (Wong, et al., (2002) *Genome Res* 12:851-856). However, most high GC mode genes and a subset of the low GC mode genes have only a slightly negative ORFGC gradient. The remaining low GC mode genes have marked negative GC gradients, but these tend to reverse to a positive GC gradient before the end of the ORF. A plot of ORF3GC (% GC codon position 3) vs GC content reveals a trimodal distribution in maize with the three classes being high GC/little gradient; low GC/little gradient; and low GC/high gradient (Simmons, et al., (2002) Maize Coop Newsletter).

The coding region can be modified to form or improve a plant initiation sequence at the 5' end of the coding region (Kozak sequence). The Kozak context is the nucleotide sequence near the start codon ATG. In maize and many cereals the preferred Kozak context is ATGG. This fourth base of the nucleic acid molecule coding sequence is dictated by the encoded second amino acid. If already present, no changes are needed. To create an ATGG Kozak context (Kozak optimization) if it does not exist, however, may result in a change to the second amino acid. For polypeptides that are N-terminus processed, such as transit peptide removal, this change would not affect the mature polypeptide. Typically the second amino acid is changed to one chemically similar properties, however, any amino acid encoded by a GXX codon can be used.

Evidence from point mutation and deletion analysis indicates that specific sequences in eukaryotes are associated with post-transcriptional processing, RNA destabilization, translational termination, intron splicing and the like. In designing a bacterial gene for expression in plants, sequences which interfere with the efficiency of gene expression are eliminated.

In modifying a polynucleotide for expression in plants, the sequence is also evaluated to identify sequences which may interfere with the efficacy of gene expression, including sequences such as any plant polyadenylation signals, termination sequences, secondary structures such as hairpins, and plant consensus splice sites may be modified. A coding region can be scanned for sequences that potentially destabilize an RNA.

Potential destabilizing sequences include plant termination and polyadenylation sequences. In eukaryotes, the primary transcripts of nuclear genes are extensively processed including, for example, 5'-capping, intron splicing, and polyadenylation, to form mature and translatable mRNAs. Polyadenylation generally involves endonucleolytic cleavage at the polyA site followed by the addition of several A residues to the cleaved end. Putative plant polyadenylation signals include AATAAA, AATGAA, AATAAT, AATATT, GATAAA, GATAAT, AATACA, TATAAA, AATATA, AATTAA, and AATAAG motifs (Joshi (1987) *Nucl Acids Res* 15:9627-9640). Termination sequences are also potentially destabilizing sequences. Polymerase II termination sequences found next to the 3' end of the US snRNA gene of *Arabidopsis thaliana* were believed to be important for transcription termination upon 3' end processing (Vankan and Filipowicz (1988) *EMBO J* 7:791-799).

Secondary structures, such as hairpins are also potentially destabilizing to an mRNA. Transcripts that form hairpin RNA structures may be more likely to be targeted for degradation and/or translational arrest. The coding sequence can be evaluated by a secondary RNA structure prediction program. Putative RNA structures predicted to be unusually stable can be disrupted by altering the sequence. Many RNA secondary structure prediction programs are known can be used. For example STEMLOOP (GCG, Accelrys, San Diego, Calif.) ranks the predicted stem-loop structures from the highest to lowest probability to form a secondary structure based on length and quality, and gives their coordinates in the sequence. The output results can then be evaluated to identify any predicted RNA structures that are unusually long and of high quality, which can then be disrupted by base changes, typically in the third codon position so as not to change amino acid sequence.

Intron splicing sites are also potential destabilization sequences. Consensus sequences for the 5' and 3' splice junctions have been derived from 20 and 30 plant intron sequences respectively (see, e.g., Brown, et al., (1986) *EMBO J* 5:2749-2758). If present, splicing of spurious introns may cause deletion of at least part of the coding region and/or a reading frame shift. The native and modified sequences can be scanned for intronic-like sequences. Intron splice-donor sites generally follow the GT-AG rule. Gene prediction software has been developed that uses sophisticated heuristics to predict which potential GT-AG combinations represent putative intron splice-donor sites (see, e.g., Brendel, et al., (2004) *Bioinformatics* 20:1157-69; Hermann, et al., (1996) *Nucl Acids Res* 24:4709-4718; Brendel, et al., (1998) *Nucl Acids Res* 26:4748-4757; Usuka, et al., (2000) *Bioinformatics* 16:203-211; Usuka, et al., (2000) *J Mol Biol* 297:1075-1085). One exemplary program is GeneSeqr (see, for example, Schlueter, et al., (2003) *Nucl Acids Res* 31:3597-3600) the output of the GeneSeqr program indicates whether there are any highly likely intron sites in the nucleic acid molecule coding sequence. Another program that can be used for this purpose is FgenesH. By using more than one program elimination of all cryptic splice sites is more likely. Removing these potential introns can be done by changing either the GT or AG sequences bordering the introns, typically without generating an amino acid substitution. Another approach to remove cryptic splice sites is to change bordering nucleotides on the putative intronic side of the putative cryptic splice site borders.

Other sequence motifs are predicted to destabilize mRNA. For example, AUUUA sequences are associated with an increased rate of mRNA degradation. The coding region, before and after modification, can be searched for any ATTTA sequence motifs and these can be altered, typically without changing the amino acid sequence. Another known destabilizing feature is downstream element (DST) mRNA destabilizing sites associated with rapid mRNA transcript degradation. DSTs are approximately 40-base sequence derived from the 3' untranslated region (UTR) of SAUR (small auxin up RNA) genes. In one study substitution mutations were made in conserved regions of the DST element containing the sequences ATAGAT and GTA, which are invariant among several SAUR genes, and reporter mRNA stability evaluated (Sullivan and Green (1996) *RNA* 2:308-315). Additionally, long poly-A or poly-T sequences may contribute to mRNA instability. Consequently, long stretches of one nucleotide, especially long stretches of A, T or combinations thereof, can be altered. The coding region, before and after modification, can be searched for any destabilizing sequence motifs and these can be altered, typically without changing the amino acid sequence.

The polynucleotide sequence of interest may be a polynucleotide sequence encoding any polynucleotide of interest, including but not limited to a polypeptide, encoding an mRNA, encoding an RNAi precursor, encoding an active RNAi agent, an antisense polynucleotide, a ribozyme, a fusion protein, a replicating vector, a screenable marker, and the like. Expression of the polynucleotide of interest may be used to induce expression of an encoding RNA and/or polypeptide, or conversely to suppress expression of an encoded RNA, RNA target sequence, and/or polypeptide. In specific examples, the polynucleotide sequence may a polynucleotide encoding a plant hormone, plant defense protein, a nutrient transport protein, a biotic association protein, a desirable input trait, a desirable output trait, a stress resistance gene, a herbicide resistance gene, a disease/pathogen resistance gene, a male sterility, a developmental gene, a regulatory gene, a DNA repair gene, a transcriptional regulatory gene, or any other polynucleotide and/or polypeptide of interest.

A number of promoters can be used in the compositions and methods. For example, a modified polynucleotide encoding a TetR polypeptide can be operably linked to a constitutive, tissue-preferred, inducible, developmentally, temporally, and/or spatially regulated, or other promoters including promoters from plant viruses or other pathogens which function in a plant cell. A variety of promoters useful in plants is reviewed in Potenza, et al., (2004) *In Vitro Cell Dev Biol Plant* 40:1-22.

Any polynucleotide, including polynucleotides of interest, modified polynucleotides encoding TetR, regulatory regions, introns, promoters, and promoters comprising TetOp sequences may be obtained, and their nucleotide sequence determined, by any standard method. The polynucleotides may be chemically synthesized in their full-length, or assembled from chemically synthesized oligonucleotides (Kutmeier, et al., (1994) *BioTechniques* 17:242). Assembly from oligonucleotides typically involves synthesis of overlapping oligonucleotides, annealing and ligating of those oligonucleotides, and PCR amplification of the ligated product. Alternatively, a polynucleotide may be isolated or generated from a suitable source including suitable source a cDNA library generated from tissue or cells, a genomic library, or directly isolated from a host by PCR amplification using specific primers to the 3' and 5' ends of the sequence, or by cloning using an nucleotide probe specific for the polynucleotide of interest. Amplified nucleic acid molecules generated by PCR may then be cloned into replicable cloning vectors using standard methods. The polynucleotide may be further manipulated using any standard methods including recombinant DNA techniques, vector construction, mutagenesis, PCR, and the like, (see, e.g., Sambrook, et al., (1990) Molecular Cloning, A Laboratory Manual, 2d Ed., Cold Spring Harbor Laboratory, Cold Spring Harbor, N.Y.; Ausubel, et al., Eds. (1998) Current Protocols in Molecular Biology, John Wiley and Sons, NY; U.S. Pat. Nos. 5,789,166 and 6,391,548).

Any method for introducing a sequence into a plant can be used, as long as the polynucleotide or polypeptide gains access to the interior of at least one cell. Methods for introducing sequences into plants are known and include, but are not limited to, stable transformation, transient transformation, virus-mediated methods, and sexual breeding. Stably incorporated indicates that the introduced polynucleotide is integrated into a genome and is capable of being inherited by progeny. Transient transformation indicates that an introduced sequence does not integrate into a genome such that it is heritable by progeny from the host. Any means can be used to bring together a TetR and polynucleotide of interest operably linked to a promoter comprising TetOp including, for example, stable transformation, transient delivery, and sexual crossing, or any combination thereof.

Transformation protocols as well as protocols for introducing polypeptides or polynucleotide sequences into plants may vary depending on the type of plant or plant cell targeted for transformation. Suitable methods of introducing polypeptides and polynucleotides into plant cells include microinjection (Crossway, et al., (1986) *Biotechniques* 4:320-334, and U.S. Pat. No. 6,300,543), electroporation (Riggs, et al., (1986) *Proc Natl Acad Sci USA* 83:5602-5606, *Agrobacterium*-mediated transformation (U.S. Pat. Nos. 5,563,055 and 5,981,840), direct gene transfer (Paszkowski, et al., (1984) *EMBO J* 3:2717-2722), ballistic particle acceleration (U.S. Pat. Nos. 4,945,050; 5,879,918; 5,886,244 and 5,932,782; Tomes, et al., (1995) in Plant Cell, Tissue, and Organ Culture: Fundamental Methods, ed. Gamborg and Phillips (Springer-Verlag, Berlin); McCabe, et al., (1988) *Biotechnology* 6:923-926). Also see, Weissinger, et al., (1988) *Ann Rev Genet* 22:421-477; Sanford, et al., (1987) *Particulate Science and Technology* 5:27-37 (onion); Christou, et al., (1988) *Plant Physiol* 87:671-674 (soybean); Finer and McMullen (1991) *In Vitro Cell Dev Biol* 27P:175-182 (soybean); Singh, et al., (1998) *Theor Appl Genet* 96:319-324 (soybean); Datta, et al., (1990) *Biotechnology* 8:736-740 (rice); Klein, et al., (1988) *Proc Natl Acad Sci USA* 85:4305-4309 (maize); Klein, et al., (1988) *Biotechnology* 6:559-563 (maize); U.S. Pat. Nos. 5,240,855; 5,322,783 and 5,324,646; Klein, et al., (1988) *Plant Physiol* 91:440-444 (maize); Fromm, et al., (1990) *Biotechnology* 8:833-839 (maize); Hooykaas-Van Slogteren, et al., (1984) *Nature* 311:763-764; U.S. Pat. No. 5,736,369 (cereals); Bytebier, et al., (1987) *Proc Natl Acad Sci USA* 84:5345-5349 (Liliaceae); De Wet, et al., (1985) in The Experimental Manipulation of Ovule Tissues, ed. Chapman et al. (Longman, New York), pp. 197-209 (pollen); Kaeppler, et al., (1990) *Plant Cell Rep* 9:415-418; Kaeppler, et al., (1992) *Theor Appl Genet* 84:560-566 (whisker-mediated transformation); D'Halluin, et al., (1992) *Plant Cell* 4:1495-1505 (electroporation); Li, et al., (1993) *Plant Cell Rep* 12:250-255; Christou and Ford (1995) *Ann Bot* 75:407-413 (rice); and Osjoda, et al., (1996) *Nat Biotechnol* 14:745-750 (maize via *A. tumefaciens*). Alternatively, polynucleotides may be introduced into plants by contacting plants with a virus, or viral nucleic acids. Methods for introducing polynucleotides into plants via viral DNA or RNA molecules are known, see, e.g., U.S. Pat. Nos. 5,889,191; 5,889,190; 5,866,785; 5,589,367; 5,316,931 and Porta, et al., (1996) *Mol Biotech* 5:209-221.

The term plant includes plant cells, plant protoplasts, plant cell tissue cultures from which a plant can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, and the like. Progeny, variants, and mutants of the regenerated plants are also included.

Any plant species can be used with the methods and compositions, including, but not limited to, monocots and dicots. Examples of plant genuses and species include, but are not limited to, corn (*Zea mays*), *Brassica* spp. (e.g., *B. napus, B. rapa, B. juncea*), castor, palm, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatas*), cassaya (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), *Arabidopsis thaliana*, oats (*Avena* spp.), barley (*Hordeum* spp.), leguminous plants such as guar beans, locust bean, fenugreek, garden beans, cowpea, mungbean, fava bean, lentils, and chickpea, vegetables, ornamentals, grasses and conifers. Vegetables include tomatoes (*Lycopersicon esculentum*), lettuce (e.g., *Lactuca sativa*), green beans (*Phaseolus vulgaris*), lima beans (*Phaseolus limensis*), peas (*Pisium* spp., *Lathyrus* spp.), and *Cucumis* species such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum. Conifers include pines, for example, loblolly pine (*Pinus taeda*), slash pine (*Pinus elliotii*), ponderosa pine (*Pinus ponderosa*), lodgepole pine (*Pinus contorta*), and Monterey pine (*Pinus radiata*), Douglas fir (*Pseudotsuga menziesii*); Western hemlock (*Tsuga canadensis*), Sitka spruce (*Picea glauca*), redwood (*Sequoia sempervirens*), true firs such as silver fir (*Abies amabilis*) and balsam fir (*Abies balsamea*), and cedars such as Western red cedar (*Thuja plicata*) and Alaska yellow cedar (*Chamaecyparis nootkatensis*).

The cells that have been transformed may be grown into plants using conventional methods (see, e.g., McCormick, et al., (1986) *Plant Cell Rep* 5:81-84). These plants may then be grown and self-pollinated, backcrossed, and/or outcrossed, and the resulting progeny having the desired characteristic identified. Two or more generations may be grown to ensure that the characteristic is stably maintained and inherited and then seeds harvested. In this manner transformed/transgenic seed having a DNA construct comprising a polynucleotide of interest and/or modified polynucleotide encoding TetR stably incorporated into their genome are provided. A plant and/or a seed having stably incorporated the DNA construct can be further characterized for expression, agronomics, and copy number.

Sequence identity may be used to compare the primary structure of two polynucleotides or polypeptide sequences, describe the primary structure of a first sequence relative to a second sequence, and/or describe sequence relationships such as variants and homologues. Sequence identity measures the residues in the two sequences that are the same when aligned for maximum correspondence. Sequence relationships can be analyzed using computer-implemented algorithms. The sequence relationship between two or more polynucleotides, or two or more polypeptides can be determined by computing the best alignment of the sequences, and scoring the matches and the gaps in the alignment, which yields the percent sequence identity, and the percent sequence similarity. Polynucleotide relationships can also be described based on a comparison of the polypeptides each encodes. Many programs and algorithms for comparison and analysis of sequences are known. Unless otherwise stated, sequence identity/similarity values provided herein refer to the value obtained using GAP Version 10 (GCG, Accelrys, San Diego, Calif.) using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix (Henikoff and Henikoff (1992) *Proc Natl Acad Sci USA* 89:10915-10919). GAP uses the algorithm of Needleman and Wunsch (1970) *J Mol Biol* 48:443-453, to find the alignment of two complete sequences that maximizes the number of matches and minimizes the number of gaps.

The properties, domains, motifs, and function of tetracycline repressor are well known as are standard techniques and assays to evaluate any tetracycline repressor comprising one or more amino acid substitutions due to codon substitution to produce a modified tetracyline repressor polynucleotide. The structure of the class D TetR protein comprises 10 alpha helices with connecting loops and turns. The 3 N-terminal helices form the DNA-binding HTH domain, which has an inverse orientation compared with HTH motifs in other DNA-binding proteins. The core of the protein, formed by helices 5-10, comprises the dimerization interface domain, and for each monomer comprises the binding pocket for ligand/effector and divalent cation cofactor (Kisker, et al., (1995) *J Mol Biol* 247:260-180; Orth, et al., (2000) *Nat Struct Biol* 7:215-219). Typically, any amino acid change will comprise a conservative substitution if possible. Conservative substitutions generally refer to exchanging one amino acid with another having similar properties and that are not expected to affect the biological activity of the protein (see, e.g., Dayhoff, et al., (1978) Atlas of Protein Sequence and Structure, Natl Biomed Res Found, Washington, D.C.). Different clustering of amino acids by similarity have been developed depending on the property evaluated, such as acidic vs. basic, polar vs. non-polar, amphipathic and the like, and be used when evaluating the possible effect of any substitution or combination of substitutions.

Numerous variants of TetR have been identified and/or derived, and extensively studied. The effects of various mutations, modifications, and/or combinations thereof have been used to extensively characterize and/or modify the properties of tetracycline repressors, such as cofactor binding, ligand binding constants, kinetics, and dissociation constants, operator binding sequence constraints, cooperativity, binding constants, kinetics, and dissociation constants, and fusion protein activities and properties. Variants include TetR variants with a reverse phenotype of binding the operator sequence in the presence of tetracycline or an analog thereof, variants having altered operator binding properties, variants having altered operator sequence specificity, and variants having altered ligand specificity, and fusion proteins. See, for example, Isackson and Bertrand (1985) *Proc Natl Acad Sci USA* 82:6226-6230; Smith and Bertrand (1988) *J Mol Biol* 203:949-959; Altschmied, et al., (1988) *EMBO J* 7:4011-4017; Wissmann, et al., (1991) *EMBO J* 10:4145-4152; Baumeister, et al., (1992) *J Mol Biol* 226:1257-1270; Baumeister, et al., (1992) *Proteins* 14:168-177; Gossen and Bujard (1992) *Proc Natl Acad Sci USA* 89:5547-5551; Wasylewski, et al., (1996) *J Protein Chem* 15:45-58; Berens, et al., (1997) *J Biol Chem* 272:6936-6942; Baron, et al., (1997) *Nucl Acids Res* 25:2723-2729; Helbl and Hillen (1998) *J Mol Biol* 276:313-318; Urlinger, et al., (2000) *Proc Natl Acad Sci USA* 97:7963-7968; Kamionka, et al., (2004) *Nucl Acids Res* 32:842-847; Bertram, et al., (2004) *J Mol Microbiol Biotechnol* 8:104-110; US Publication Number 2003/0186281.

The three-dimensional structures of tetracycline repressors, tetracycline repressor variants, coupled to ligand and/or co-factor(s), and bound to operator sequence are known (see, for example, Kisker, et al., (1995) *J Mol Biol* 247:260-280; Orth, et al., (1998) *J Mol Biol* 279:439-447; Orth, et al., (1999) *Biochemistry* 38:191-198; Orth, et al., (2000) *Nat Struct Biol* 7:215-219) providing extremely well characterized structure(s), identification of domains and individual amino acids associated with various functions and binding properties, and predictive model(s) for the potential effects of any amino acid substitution(s), as well as the possible structural bases for the phenotype(s) of known tetracycline repressor mutants.

EXAMPLES

Example 1

Modifying Tetracycline Repressor Coding Sequence

The native tetracycline repressor coding sequence from *E. coli* (SEQ ID NO: 1) was evaluated to identify any potential sequences that may affect its expression in maize. For example, codon usage differences between *E. coli* and *Z. mays* and their relevance towards effective translation in maize was examined, as well as Kozak sequence, GC content, putative cryptic intron sites, open reading frames, premature polyadenylation signals, RNA instability sites, and RNA secondary structure. After any modifications, the modified sequence was re-evaluated using the same analyses and criteria to confirm that no possibly deleterious or destabilizing changes had been introduced.

The modification of TetR had several overall objectives including:

1) replace codons rarely used in maize with more frequently used codons;

2) increase GC content by codon substitution with codons having G or C in position 3

3) apply codon changes as conservatively as possible while still achieving 1 and 2 above; and, 4) eliminate predicted RNA signals potentially deleterious to expression.

While there was no prediction on how much codon changes would impact expression, it was expected that overall GC content and spurious RNA signals would impact expression negatively. An example of a particularly rare codon in maize is the TTA codon for leucine, which has a frequency of usage less than about 10% (0.1) based on available maize codon tables. The native TetR gene contains 16 TTA codons, or about half of the total 33 leucine residues in the protein. These TTA codons were specifically targeted for substitution with other codons for leucine having a higher frequency of use in maize. Many of the additional codon substitutions were made to increase overall GC content of the coding sequence. The evaluation of codon usage in *E. coli* TetR polynucleotide (SEQ ID NO: 1) as compared to maize is shown in Table 3.

TABLE 3

| AA | Codon | Maize Codon Freq | TetR Codon Freq | TetR vs. Maize |
|---|---|---|---|---|
| Ala | GCA | 0.24 | 0.31 | 0.07 |
|  | GCC | 0.28 | 0.31 | 0.03 |
|  | GCG | 0.21 | 0 | −0.21 |
|  | GCT | 0.28 | 0.38 | 0.10 |
| Arg | AGA | 0.18 | 0.20 | 0.02 |
|  | AGG | 0.17 | 0.20 | 0.03 |
|  | CGA | 0.15 | 0.10 | −0.05 |
|  | CGC | 0.20 | 0.10 | −0.10 |
|  | CGG | 0.16 | 0.20 | 0.04 |
|  | CGT | 0.13 | 0.20 | 0.07 |
| Asn | AAC | 0.52 | 0.29 | −0.23 |
|  | AAT | 0.48 | 0.71 | 0.23 |
| Asp | GAC | 0.49 | 0.12 | −0.37 |
|  | GAT | 0.51 | 0.88 | 0.37 |
| Cys | TGC | 0.59 | 0.67 | 0.08 |
|  | TGT | 0.41 | 0.33 | −0.08 |
| Gln | CAA | 0.51 | 0.75 | 0.24 |
|  | CAG | 0.49 | 0.25 | −0.24 |
| Glu | GAA | 0.47 | 0.67 | 0.20 |
|  | GAG | 0.53 | 0.33 | −0.20 |
| Gly | GGA | 0.29 | 0.23 | −0.06 |
|  | GGC | 0.31 | 0.08 | −0.23 |
|  | GGG | 0.20 | 0.23 | 0.03 |
|  | GGT | 0.20 | 0.46 | 0.26 |
| His | CAC | 0.48 | 0.33 | −0.15 |
|  | CAT | 0.52 | 0.67 | 0.15 |
| Ile | ATA | 0.22 | 0.17 | −0.05 |
|  | ATC | 0.44 | 0.50 | 0.06 |
|  | ATT | 0.35 | 0.33 | −0.02 |
| Leu | CTA | 0.11 | 0.09 | −0.02 |
|  | CTC | 0.23 | 0.12 | −0.11 |
|  | CTG | 0.24 | 0.03 | −0.21 |
|  | CTT | 0.20 | 0.09 | −0.11 |
|  | TTA | 0.08 | 0.55 | 0.47 |
|  | TTG | 0.15 | 0.12 | −0.03 |
| Lys | AAA | 0.39 | 0.83 | 0.44 |
|  | AAG | 0.61 | 0.17 | −0.44 |
| Met | ATG | 1.00 | 1.00 | 0 |
| Phe | TTC | 0.58 | 0.22 | −0.36 |
|  | TTT | 0.42 | 0.78 | 0.36 |
| Pro | CCA | 0.28 | 0.29 | 0.01 |
|  | CCC | 0.21 | 0 | −0.21 |
|  | CCG | 0.24 | 0.14 | −0.10 |
|  | CCT | 0.27 | 0.57 | 0.30 |
| Stop | TAA | 0.21 | 1.00 | 0.79 |
|  | TAG | 0.17 | 0 | −0.17 |
|  | TGA | 0.62 | 0 | −0.62 |
| Ser | AGC | 0.21 | 0.27 | 0.06 |
|  | AGT | 0.13 | 0.45 | 0.32 |
|  | TCA | 0.17 | 0.09 | −0.08 |
|  | TCC | 0.19 | 0 | −0.19 |
|  | TCG | 0.13 | 0 | −0.13 |
|  | TCT | 0.18 | 0.18 | 0 |
| Thr | ACA | 0.27 | 0.45 | 0.18 |
|  | ACC | 0.29 | 0.09 | −0.20 |
|  | ACG | 0.20 | 0 | −0.20 |
|  | ACT | 0.24 | 0.45 | 0.21 |
| Trp | TGG | 1.00 | 1.00 | 0 |
| Tyr | TAC | 0.54 | 0 | −0.54 |
|  | TAT | 0.46 | 1.00 | 0.54 |
| Val | GTA | 0.14 | 0.50 | 0.36 |
|  | GTC | 0.29 | 0.25 | −0.04 |
|  | GTG | 0.31 | 0.25 | −0.06 |
|  | GTT | 0.27 | 0 | −0.27 |

In considering mRNA stability, sequences were evaluated for the presence of destabilization (DST) sites, stretches of A's or T's, and the ATTTA RNA destabilization site. The *E. coli* TetR coding sequence has many stretches of A's and Ts, one ATTTA site, several closely related sites, and no DST sites. These findings suggest potential mRNA instability in plants in general, including maize.

The canonical polyA adenylation signal in maize is AATAAA, and related sequences. Sequence regions of three contiguous A's may potentially act as a spurious polyA signal. Several regions of *E. coli* TetR coding region having AAA were identified as potential regions for sequence modification by codon substitution. No exact matches to the AATAAA signal were identified, but closely related sequences were identified and targeted for potential modification.

After analysis of the *E. coli* sequence, the TetRMOD1 (SEQ ID NO: 3) modified sequence comprising minimal proposed codon substitutions was re-evaluated, and any further sequence substitutions made to remove or reduce any potentially deleterious sequence and/or signals to produce TetRMOD2 (SEQ ID NO: 13). Each round of modification was followed by re-evaluation of the sequence produced, such that modified sequences TetRMOD3 (SEQ ID NO: 5) and TetMOD4 (SEQ ID NO: 11) were also generated.

In *E. coli* TetR and TetRMOD1 the second codon is serine, so that the first 6 nucleotides of the coding region are ATGTCT. Changing the second codon to a codon beginning with G would produce the preferred translational start context for maize, which is ATGGc. Five amino acids have codons beginning with G: glycine, alanine, valine, aspartic acid, and glutamic Acid. Of these, alanine is chemically most similar to serine, and a GCX codon produces the most preferred Kozak context for maize. TetRMOD1 was examined for spurious intron splicing signal sequences. FgenesH predicted no intron. GeneSeqr predicted a possible intron with two possible acceptor sites which were eliminated by codon changes. These additional codon substitutions were introduced, and convenient restriction sites added to generate TetRMOD3 (SEQ ID NO: 5) and TetRMOD4 (SEQ ID NO: 11). The isolated polynucleotide TetRMOD4 (SEQ ID NO: 11) was synthesized at GenScript Corp. (Piscataway, N.J., USA) prior to incorporating it into maize expression cassettes for transformation.

The overall GC content for *E. coli* TetR (SEQ ID NO: 1) of 40.4% was low as compared to typical maize genes, particularly nuclear-encoded genes. After sequence modification by codon substitution to produce TetMOD3 (SEQ ID NO: 5) the overall GC content was increased to about 53.5%. The modified coding sequence results in only one amino acid substitution, serine at position 2 is changed to alanine after sequence modification to improve the Kozak translation initiation sequence context (SEQ ID NO: 6). Minimal codon substitutions were made, overall 77 codon substitutions were made to the native *E. coli* coding region, of these 53 codon substitutions comprise substituting the codon with the highest frequency of use in maize.

Table 4 shows a PILEUP (GCG, Accelrys, San Diego, Calif.) alignment of modified sequences TetRMOD1-4 (SEQ ID NOS: 3, 13, 5 and 11) with the native *E. coli* TetR polynucleotide (SEQ ID NO: 1), and the polypeptide(s) encoded. Base substitutions are shown in bold, and the position noted by an asterick (*). Conserved protein domains are italicized or underlined and noted in the right margin. The structure of the class D TetR protein comprises 10 alpha helices with connecting loops and turns. The 3 N-terminal helices form the DNA-binding HTH domain, which has an inverse orientation compared with HTH motifs in other DNA-binding proteins. The core of the protein, formed by helices 5-10, comprises the dimerization interface domain, and for each monomer comprises the binding pocket for ligand/effector and divalent cation cofactor (Kisker, et al., (1995) *J Mol Biol* 247:260-180; Orth, et al., (2000) *Nat Struct Biol* 7:215-219). Conserved domains include the Pfam TetR_N domain which is a conserved 47 amino acid domain in the N-terminal region of the tetracycline repressor family of proteins, it is shown in bold italicized font in TABLE 4. The Pfam TetR_C domain is a conserved 134 amino acid domain comprising the core of the protein, shown in bold underlined font in TABLE 4.

TABLE 4

PileUP

```
                         *  *    * * *  *  *     *           * *
TetRMOD1        ATGTCTAGACTCGACAAGAGCAAGGTGATCAACAGCGCACTCGAGCTGCT
SEQ ID NO: 3

TetRMOD2        atgtctagactcgacaagagcaaggtgatcaacagcgcactcgagctgct
SEQ ID NO: 13

TetRMOD3        ATGGCCAGACTCGACAAGAGCAAGGTGATCAACAGCGCACTCGAGCTGCT
SEQ ID NO: 5

TetRMOD4        atggccagactcgacaagagcaaggtgatcaacagcgcactggagctgct
SEQ ID NO: 11

TetR            ATGTCTAGATTAGATAAAAGTAAAGTGATTAACAGCGCATTAGAGCTGCT
SEQ ID NO: 1    MetSerArgLeuAspLysSerLys ValIle AsnSer AlaLeu GluLeuLe

TetR_N
                        ALA

*  *                        ** *
TetRMOD1        GAACGAGGTCGGAATCGAAGGCCTCACAACCCGTAAACTCGCCCAGAAGC
TetRMOD2        gaacgaggtcggaatcgaaggcctcacaacccgtaaactcgcccagaagc
TetRMOD3        GAACGAGGTCGGAATCGAAGGCCTCACAACCCGTAAACTCGCCCAGAAGC
TetRMOD4        gaacgaggtcggaatcgaaggcctcacaacccgtaaactcgcccagaagc
TetR            TAATGAGGTCGGAATCGAAGGTTTAACAACCCGTAAACTCGCCCAGAAGC
                uAsnGluValGlyIleGluGlyLe uThrTh rArgLy LeuALaGlnLysL TetR_N

*  *                  *     *  * *    *
TetRMOD1        TCGGTGTAGAGCAGCCTACATTGTATTGGCATGTCAAGAACAAGCGGGCT
TetRMOD2        tcggtgtagagcagcctacattgtattggcacgtcaagaacaagcgggct
TetRMOD3        TCGGGGTAGAGCAGCCTACATTGTATTGGCATGTCAAGAACAAGCGGGCT
TetRMOD4        tcggggtagagcagcctacattgtattggcacgtcaagaacaagcgggct
TetR            TAGGTGTAGAGCAGCCTACATTGTATTGGCATGTAAAAAATAAGCGGGCT
                euGlyVa lGluGln ProTh rLeuTy rTrpHisValLy sAsnLy sArgAla TetR_N

*    *  *        *  *              *
TetRMOD1        TTGCTCGACGCCCTCGCCATTGAGATGCTCGATAGGCACCATACCCACTT
TetRMOD2        ttgctagacgccctcgccattgagatgctcgataggcaccatacccactt
TetRMOD3        TTGCTCGACGCCCTCGCCATTGAGATGCTCGATAGGCACCATACCCACTT
TetRMOD4        ttgctagacgccctcgccattgagatgctcgataggcaccatacccactt
TetR            TTGCTCGACGCCTTAGCCATTGAGATGTTAGATAGGCACCATACTCACTT
                LeuLeu AspAla LeuAlaIleGluMetLeuAspArgHisHisThrHisPh TetR_N

*      *             *  * *  *
TetRMOD1        CTGCCCTTTGGAAGGGGAAAGCTGGCAAGACTTCCTGCGCAACAACGCTA
TetRMOD2        ctgcccttiggaaggggaaagctggcaagacttcttgaggaacaacgcta
TetRMOD3        CTGCCCTTTGGAAGGGGAAAGCTGGCAAGACTTCCTGCGCAACAACGCTA
TetRMOD4        ctgcccttiggaaggggaaagctggcaagacttcttgaggaacaacgcta
TetR            TTGCCCTTTAGAAGGGGAAAGCTGGCAAGATTTTTTACGTAATAACGCTA
                eCysProLeuGluGlyGluSerTrpGlnAspPheLeuArgAsnAsnAlaL TetR_C

* *           *        *  *         * * *  *
TetRMOD1        AGAGCTTCAGATGTGCTTTGCTCAGTCATCGCGATGGAGCCAAGGTCCAC
TetRMOD2        agagcttcagatgtgctttgctcagtcatcgcgatggagccaaggtccac
TetRMOD3        AGAGCTTCAGATGTGCTTTGCTCAGTCATCGCGATGGAGCCAAGGTCCAC
TetRMOD4        agagcttcagatgtgctttgctcagtcaccgtgatggagccaaggtccac
TetR            AAAGTTTTAGATGTGCTTTACTAAGTCATCGCGATGGAGCAAAAGTACAT
                ysSerPheArgCysAlaLeuLeuSerHisArgAspGlyAlaLysValHis TetR_C

* *         *  *  *              * *  *
TetRMOD1        TTGGGTACACGGCCTACAGAGAAGCAGTATGAAACTCTCGAGAACCAGCT
TetRMOD2        ttgggtacacggcctacagagaagcagtatgaaactctcgagaaccagct
TetRMOD3        TTGGGTACACGGCCTACGGAGAAGCAGTATGAAACTCTCGAGAACCAGCT
```

TABLE 4-continued

PileUP

```
TetRMOD4   ctaggtacacggcctacggagaagcagtatgaaactctcgagaaccagct
TetR       TTAGGTACACGGCCTACAGAAAAACAGTATGAAACTCTCGAAAATCAATT
           LeuGlyThrArgProThrGluLysGlnThrGluThrLeuGluAsnGlnLe TetR_C

*    ** *              *   *          ** *   *
TetRMOD1   CGCCTTCCTGTGCCAACAAGGTTTCTCCCTTGAGAATGCCCTCTACGCAC
TetRMOD2   cgccttcctgtgccaacaaggtttctcccttgagaatgccctctacgcac
TetRMOD3   CGCCTTCCTGTGCCAACAAGGTTTCTCCCTTGAGAATGCCCTCTACGCAC
TetRMOD4   cgccttcctgtgccaacaaggtttctcccttgagaatgccctctacgcac
TetR       AGCCTTTTTATGCCAACAAGGTTTTTCACTAGAGAATGCATTATATGCAC
           uAlaPheLeuCysGlnGlnGlyPheSerLeuGluAsnAlaLeuTyrAlaL TetR_C

**        *       *   *  *  *
TetRMOD1   TCAGCGCTGTGGGGCACTTCACTCTGGGTTGCGTATTGGAAGATCAAGAG
TetRMOD2   tcagcgctgtagggcacttcactctgggttgcgtattggaagatcaagag
TetRMOD3   TCTCCGCTGTGGGGCACTTCACTCTGGGTTGCGTATTGGAAGATCAAGAG
TetRMOD4   tctccgctgtagggcacttcactctgggttgcgtattggaagatcaagag
TetR       TCAGCGCTGTGGGGCATTTTACTTTAGGTTGCGTATTGGAAGATCAAGAG
           euSerAlaValGlyHisPheThrLeuGlyCysValLeuGluAspGlnGlu TetR_C 10              *   *  *
TetRMOD1   CATCAAGTCGCTAAGGAGGAGAGGGAAACACCTACTACTGATAGTATGCC
TetRMOD2   catcaagtcgctaaggaggagagggaaacacctactactgatagtatgcc
TetRMOD3   CATCAAGTCGCTAAGGAGGAGAGGGAAACACCTACTACTGATAGTATGCC
TetRMOD4   caccaagtcgctaaggaggagagggaaacacctactactgatagtatgcc
TetR       CATCAAGTCGCTAAAGAAGAAAGGGAAACACCTACTACTGATAGTATGCC
           HisGlnValAlaLysGluGluArgGluThrProThrThrAspSerMetPr TetR_C

*  **  *               ** *    *
TetRMOD1   GCCACTGCTCCGACAAGCTATCGAGCTCTTCGATCACCAAGGTGCAGAGC
TetRMOD2   gccactgctccgacaagctatcgagctcttcgatcaccaaggtgcagagc
TetRMOD3   GCCACTGCTCCGACAAGCTATCGAGCTCTTCGATCACCAAGGTGCAGAGC
TetRMOD4   gccactgctccgacaagctatcgagctcttcgatcaccaaggtgcagagc
TetR       GCCATTATTACGACAAGCTATCGAATTATTTGATCACCAAGGTGCAGAGC
           oProLeuLeuArgGlnAlaIleGluLeuPheAspHisGlnGlyAlaGluP TetR_C

* *                          *   *  *  *
TetRMOD1   CAGCCTTCCTGTTCGGCCTTGAATTGATCATATGCGGATTGGAGAAGCAG
TetRMOD2   cagccttcctgttcggccttgaattgatcatatgcggattggagaagcag
TetRMOD3   CAGCCTTCCTGTTCGGCCTTGAATTGATCATATGCGGATTGGAGAAGCAG
TetRMOD4   cagccttcctgttcggccttgaattgatcatatgcggattggagaagcag
TetR       CAGCCTTCTTATTCGGCCTTGAATTGATCATATGCGGATTAGAAAAACAA
           roAlaPheLeuPheGlyLeuGluLeuIleIleCysGlyLeuGluLysGln TetR_C 10    *
TetRMOD1   CTGAAGTGTGAAAGTGGGTCTTAA
TetRMOD2   ctgaagtgtgaaagtgggtcttaa
TetRMOD3   CTGAAGTGTGAAAGTGGGTCTTAA
TetRMOD4   ctgaagtgtgaaagtgggtcttaa
TetR       CTTAAATGTGAAAGTGGGTCTTAA
           LeuLysCysGluSerGlySerSTP TetR_C
```

Exemplary sequence modifications are shown in Table 5, wherein unmodified codons are listed under "*E. coli*" heading in lowercase (SEQ ID NOS: 1 and 2), modified codons are listed in uppercase bolded type, and TetRMOD3 (SEQ ID NOS: 5 and 6) only lists the codons that are changed in that exemplary modified sequence.

TABLE 5

| Codon | *E. coli* | AA | Freq. | TetRMOD3 | AA | Freq |
|---|---|---|---|---|---|---|
| 1 | atg | M | 1.0 | | | |
| 2 | TCT | S | 0.18 | GCC | A | 0.28 |
| 3 | aga | R | 0.18 | | | |
| 4 | TTA | L | 0.08 | CTC | L | 0.23 |
| 5 | GAT | D | 0.51 | GAC | D | 0.49 |
| 6 | AAA | K | 0.39 | AAG | K | 0.61 |
| 7 | AGT | S | 0.13 | AGC | S | 0.21 |
| 8 | AAA | K | 0.39 | AAG | K | 0.61 |
| 9 | gtg | V | 0.31 | | | |
| 10 | ATT | I | 0.35 | ATC | I | 0.44 |
| 11 | aac | N | 0.52 | | | |
| 12 | agc | S | 0.21 | | | |
| 13 | gca | A | 0.24 | | | |
| 14 | TTA | L | 0.08 | CTG | L | 0.24 |
| 15 | gag | E | 0.53 | | | |
| 16 | ctg | L | 0.24 | | | |
| 17 | CTT | L | 0.20 | CTG | L | 0.24 |
| 18 | AAT | N | 0.48 | AAC | N | 0.52 |
| 19 | gag | E | 0.53 | | | |
| 20 | gtc | V | 0.29 | | | |
| 21 | gga | G | 0.29 | | | |
| 22 | atc | I | 0.44 | | | |
| 23 | gaa | E | 0.47 | | | |
| 24 | GGT | G | 0.20 | GGC | G | 0.31 |
| 25 | TTA | L | 0.08 | CTC | L | 0.23 |
| 26 | aca | T | 0.27 | | | |
| 27 | acc | T | 0.29 | | | |
| 28 | cgt | R | 0.13 | | | |
| 29 | aaa | K | 0.39 | | | |
| 30 | ctc | L | 0.23 | | | |
| 31 | gcc | A | 0.28 | | | |
| 32 | cag | Q | 0.49 | | | |
| 33 | aag | K | 0.61 | | | |
| 34 | CTA | L | 0.11 | CTC | L | 0.23 |
| 35 | GGT | G | 0.20 | GGG | G | 0.20 |
| 36 | gta | V | 0.14 | | | |
| 37 | gag | E | 0.53 | | | |
| 38 | cag | Q | 0.49 | | | |
| 39 | cct | P | 0.27 | | | |
| 40 | aca | T | 0.27 | | | |
| 41 | ttg | L | 0.15 | | | |
| 42 | tat | Y | 0.46 | | | |
| 43 | tgg | W | 1.0 | | | |
| 44 | CAT | H | 0.52 | CAC | H | 0.48 |
| 45 | GTA | V | 0.14 | GTC | V | 0.29 |
| 46 | AAA | K | 0.39 | AAG | K | 0.61 |
| 47 | AAT | N | 0.48 | AAC | N | 0.52 |
| 48 | aag | K | 0.61 | | | |
| 49 | cgg | R | 0.16 | | | |
| 50 | gct | A | 0.28 | | | |
| 51 | ttg | L | 0.15 | | | |
| 52 | CTC | L | 0.23 | CTA | L | 0.11 |
| 53 | gac | D | 0.49 | | | |
| 54 | gcc | A | 0.28 | | | |
| 55 | TTA | L | 0.08 | CTC | L | 0.23 |
| 56 | gcc | A | 0.28 | | | |
| 57 | att | I | 0.35 | | | |
| 58 | gag | E | 0.53 | | | |
| 59 | atg | M | 1.0 | | | |
| 60 | TTA | L | 0.08 | CTC | L | 0.23 |
| 61 | gat | D | 0.51 | | | |
| 62 | agg | R | 0.17 | | | |
| 63 | cac | H | 0.48 | | | |
| 64 | cat | H | 0.52 | | | |
| 65 | ACT | T | 0.24 | ACC | T | 0.29 |
| 66 | cac | H | 0.48 | | | |
| 67 | TTT | F | 0.42 | TTC | F | 0.58 |
| 68 | tgc | C | 0.59 | | | |
| 69 | cct | P | 0.27 | | | |
| 70 | TTA | L | 0.08 | TTG | L | 0.15 |
| 71 | gaa | E | 0.47 | | | |
| 72 | ggg | G | 0.20 | | | |
| 73 | gaa | E | 0.47 | | | |
| 74 | agc | S | 0.21 | | | |
| 75 | tgg | W | 1.0 | | | |
| 76 | caa | Q | 0.51 | | | |
| 77 | GAT | D | 0.51 | GAC | D | 0.49 |
| 78 | TTT | F | 0.42 | TTC | F | 0.58 |
| 79 | TTA | L | 0.08 | TTG | L | 0.15 |
| 80 | CGT | R | 0.13 | AGG | R | 0.17 |
| 81 | AAT | N | 0.48 | AAC | N | 0.52 |
| 82 | aac | N | 0.52 | | | |
| 83 | gct | A | 0.28 | | | |
| 84 | AAA | K | 0.39 | AAG | K | 0.61 |
| 85 | AGT | S | 0.13 | AGC | S | 0.21 |
| 86 | TTT | F | 0.42 | TTC | F | 0.58 |
| 87 | aga | R | 0.18 | | | |
| 88 | tgt | C | 0.41 | | | |
| 89 | gct | A | 0.28 | | | |
| 90 | TTA | L | 0.08 | TTG | L | 0.15 |
| 91 | CTA | L | 0.11 | CTC | L | 0.23 |
| 92 | agt | S | 0.13 | | | |
| 93 | CAT | H | 0.52 | CAC | H | 0.48 |
| 94 | CGC | R | 0.20 | CGT | R | 0.13 |
| 95 | gat | D | 0.51 | | | |
| 96 | gga | G | 0.29 | | | |
| 97 | GCA | A | 0.24 | GCC | A | 0.28 |
| 98 | AAA | K | 0.39 | AAG | K | 0.61 |
| 99 | GTA | V | 0.14 | GTC | V | 0.29 |
| 100 | CAT | H | 0.52 | CAC | H | 0.48 |
| 101 | TTA | L | 0.08 | CTA | L | 0.11 |
| 102 | ggt | G | 0.20 | | | |
| 103 | aca | T | 0.27 | | | |
| 104 | cgg | R | 0.16 | | | |
| 105 | cct | P | 0.27 | | | |
| 106 | ACA | T | 0.27 | ACG | T | 0.20 |
| 107 | GAA | E | 0.47 | GAG | E | 0.53 |
| 108 | AAA | K | 0.39 | AAG | K | 0.61 |
| 109 | cag | Q | 0.49 | | | |
| 110 | tat | Y | 0.46 | | | |
| 111 | gaa | E | 0.47 | | | |
| 112 | act | T | 0.24 | | | |
| 113 | ctc | L | 0.23 | | | |
| 114 | GAA | E | 0.47 | GAG | E | 0.53 |
| 115 | AAT | N | 0.48 | AAC | N | 0.52 |
| 116 | CAA | Q | 0.51 | CAG | Q | 0.49 |
| 117 | TTA | L | 0.08 | CTC | L | 0.23 |
| 118 | gcc | A | 0.28 | | | |
| 119 | TTT | F | 0.42 | TTC | F | 0.58 |
| 120 | TTA | L | 0.08 | CTG | L | 0.24 |
| 121 | tgc | C | 0.59 | | | |
| 122 | caa | Q | 0.51 | | | |
| 123 | caa | Q | 0.51 | | | |
| 124 | ggt | G | 0.20 | | | |
| 125 | TTT | F | 0.42 | TTC | F | 0.58 |
| 126 | TCA | S | 0.17 | TCC | S | 0.19 |
| 127 | CTA | L | 0.11 | CTT | L | 0.20 |
| 128 | gag | E | 0.53 | | | |
| 129 | aat | N | 0.48 | | | |
| 130 | GCA | A | 0.24 | GCC | A | 0.28 |
| 131 | TTA | L | 0.08 | CTC | L | 0.23 |
| 132 | TAT | Y | 0.46 | TAC | Y | 0.54 |
| 133 | gca | A | 0.24 | | | |
| 134 | ctc | L | 0.23 | | | |
| 135 | AGC | S | 0.21 | TCC | S | 0.19 |
| 136 | gct | A | 0.28 | | | |
| 137 | GTG | V | 0.31 | GTA | V | 0.14 |
| 138 | ggg | G | 0.20 | | | |
| 139 | CAT | H | 0.52 | CAC | H | 0.48 |
| 140 | TTT | F | 0.42 | TTC | F | 0.58 |
| 141 | act | T | 0.24 | | | |
| 142 | TTA | L | 0.08 | CTG | L | 0.24 |
| 143 | ggt | G | 0.20 | | | |
| 144 | tgc | C | 0.59 | | | |
| 145 | gta | V | 0.14 | | | |
| 146 | ttg | L | 0.15 | | | |
| 147 | gaa | E | 0.47 | | | |

TABLE 5-continued

| Codon | E. coli | AA | Freq. | TetRMOD3 | AA | Freq |
|---|---|---|---|---|---|---|
| 148 | gat | D | 0.51 | | | |
| 149 | caa | Q | 0.51 | | | |
| 150 | gag | E | 0.53 | | | |
| 151 | CAT | H | 0.52 | CAC | H | 0.48 |
| 152 | caa | Q | 0.51 | | | |
| 153 | gtc | V | 0.29 | | | |
| 154 | gct | A | 0.28 | | | |
| 155 | AAA | K | 0.39 | AAG | K | 0.61 |
| 156 | GAA | E | 0.47 | GAG | E | 0.53 |
| 157 | GAA | E | 0.47 | GAG | E | 0.53 |
| 158 | agg | R | 0.17 | | | |
| 159 | gaa | E | 0.47 | | | |
| 160 | aca | T | 0.27 | | | |
| 161 | cct | P | 0.27 | | | |
| 162 | act | T | 0.24 | | | |
| 163 | act | T | 0.24 | | | |
| 164 | gat | D | 0.51 | | | |
| 165 | agt | S | 0.13 | | | |
| 166 | atg | M | 1.0 | | | |
| 167 | ccg | P | 0.24 | | | |
| 168 | cca | P | 0.28 | | | |
| 169 | TTA | L | 0.08 | CTG | L | 0.24 |
| 170 | TTA | L | 0.08 | CTC | L | 0.23 |
| 171 | cga | R | 0.15 | | | |
| 172 | caa | Q | 0.51 | | | |
| 173 | gct | A | 0.28 | | | |
| 174 | atc | I | 0.44 | | | |
| 175 | GAA | E | 0.47 | GAG | E | 0.53 |
| 176 | TTA | L | 0.08 | CTC | L | 0.23 |
| 177 | TTT | F | 0.42 | TTC | F | 0.58 |
| 178 | gat | D | 0.51 | | | |
| 179 | cac | H | 0.48 | | | |
| 180 | caa | Q | 0.51 | | | |
| 181 | ggt | G | 0.20 | | | |
| 182 | gca | A | 0.24 | | | |
| 183 | gag | E | 0.53 | | | |
| 184 | cca | P | 0.28 | | | |
| 185 | gcc | A | 0.28 | | | |
| 186 | ttc | F | 0.58 | | | |
| 187 | TTA | L | 0.08 | CTG | L | 0.24 |
| 188 | ttc | F | 0.58 | | | |
| 189 | ggc | G | 0.31 | | | |
| 190 | ctt | L | 0.20 | | | |
| 191 | gaa | E | 0.47 | | | |
| 192 | ttg | L | 0.15 | | | |
| 193 | atc | I | 0.44 | | | |
| 194 | ata | I | 0.22 | | | |
| 195 | tgc | C | 0.59 | | | |
| 196 | gga | G | 0.29 | | | |
| 197 | TTA | L | 0.08 | TTG | L | 0.15 |
| 198 | GAA | E | 0.47 | GAG | E | 0.53 |
| 199 | AAA | K | 0.39 | AAG | K | 0.61 |
| 200 | CAA | Q | 0.51 | CAG | Q | 0.49 |
| 201 | CTT | L | 0.20 | CTG | L | 0.24 |
| 202 | AAA | K | 0.39 | AAG | K | 0.61 |
| 203 | tgt | C | 0.41 | | | |
| 204 | gaa | E | 0.47 | | | |
| 205 | agt | S | 0.13 | | | |
| 206 | ggg | G | 0.20 | | | |
| 207 | tct | S | 0.18 | | | |

Blank = no codon substitution

A brief comparison of E. coli TetR (SEQ ID NO: 1) and modified sequence TetRMOD3 (SEQ ID NO: 5) is shown in Table 6, numbers are based on the maize codon frequencies shown in Table 1, and the total of 207 codons in each sequence.

TABLE 6

| | | # Codon (% total) | | | | |
|---|---|---|---|---|---|---|
| | % GC | Freq <0.2 | Freq ≧0.2 | Most freq codon | Total codons changed | Total changed to most Freq | Total changed having higher % GC |
| E. coli | 40.3 | 46 (22.2%) | 161 (77.8%) | 69 (33.4%) | — | — | — |
| TetRMOD3 | 53.5 | 29 (14.0%) | 178 (86.0%) | 99 (47.8%) | 77 (37.2%) | 42 (20.3%) | 70 (33.8%) |

Sequence alignments and percent sequence identity and similarity were generated using the GAP algorithm (GCG, Accelrys, San Diego, Calif. USA) under default parameters: comparison table=nwsgapdna.cmp; Gap weight=50; length weight=3. Table 7 summarizes the pairwise percent sequence identity between modified and unmodified TetR polynucleotides. Table 8 gives the GAP analysis output for each comparison.

TABLE 7

GAP analysis of TetR polynucleotides % identity

| Sequence | TetRMod1 | TetRMod2 | TetRMod3 | TetRMod4 | TetR |
|---|---|---|---|---|---|
| TetRMod1 | 100 | 99.038 | 99.038 | 97.115 | 87.019 |
| TetRMod2 | | 100 | 98.077 | 98.077 | 86.538 |
| TetRMod3 | | | 100 | 98.077 | 86.058 |
| TetRMod4 | | | | 100 | 85.096 |

TABLE 8

A. TetRMOD1 × TetRMOD2 (SEQ ID NO: 3 × SEQ ID NO: 13)

| | | | |
|---|---|---|---|
| Quality: | 6180 | Length: | 624 |
| Ratio: | 9.904 | Gaps: | 0 |
| Percent Similarity: | 99.038 | Percent Identity: | 99.038 |

```
  1 ATGTCTAGACTCGACAAGAGCAAGGTGATCAACAGCGCACTCGAGCTGCT 50
    ||||||||||||||||||||||||||||||||||||||||||||||||||
  1 atgtctagactcgacaagagcaaggtgatcaacagcgcactcgagctgct 50

51 GAACGAGGTCGGAATCGAAGGCCTCACAACCCGTAAACTCGCCCAGAAGC 100
    ||||||||||||||||||||||||||||||||||||||||||||||||||
 51 gaacgaggtcggaatcgaaggcctcacaacccgtaaactcgcccagaagc 100

101 TCGGTGTAGAGCAGCCTACATTGTATTGGCATGTCAAGAACAAGCGGGCT 150
    |||||||||||||||||||||||||||||||| |||||||||||||||||
101 tcggtgtagagcagcctacattgtattggcacgtcaagaacaagcgggct 150

151 TTGCTCGACGCCCTCGCCATTGAGATGCTCGATAGGCACCATACCCACTT 200
    ||||| ||||||||||||||||||||||||||||||||||||||||||||
151 ttgctagacgccctcgccattgagatgctcgataggcaccatacccactt 200

201 CTGCCCTTTGGAAGGGGAAAGCTGGCAAGACTTCCTGCGCAACAACGCTA 250
    |||||||||||||||||||||||||||||||||| || | ||||||||||
201 ctgccctttggaaggggaaagctggcaagacttcttgaggaacaacgcta 250

251 AGAGCTTCAGATGTGCTTTGCTCAGTCATCGCGATGGAGCCAAGGTCCAC 300
    ||||||||||||||||||||||||||||||||||||||||||||||||||
251 agagcttcagatgtgctttgctcagtcatcgcgatggagccaaggtccac 300

301 TTGGGTACACGGCCTACAGAGAAGCAGTATGAAACTCTCGAGAACCAGCT 350
    ||||||||||||||||||||||||||||||||||||||||||||||||||
301 ttgggtacacggcctacagagaagcagtatgaaactctcgagaaccagct 350

351 CGCCTTCCTGTGCCAACAAGGTTTCTCCCTTGAGAATGCCCTCTACGCAC 400
    ||||||||||||||||||||||||||||||||||||||||||||||||||
351 cgccttcctgtgccaacaaggtttctcccttgagaatgccctctacgcac 400

401 TCAGCGCTGTGGGGCACTTCACTCTGGGTTGCGTATTGGAAGATCAAGAG 450
    |||||||||| |||||||||||||||||||||||||||||||||||||||
401 tcagcgctgtagggcacttcactctgggttgcgtattggaagatcaagag 450

451 CATCAAGTCGCTAAGGAGGAGAGGGAAACACCTACTACTGATAGTATGCC 500
    ||||||||||||||||||||||||||||||||||||||||||||||||||
451 catcaagtcgctaaggaggagagggaaacacctactactgatagtatgcc 500

501 GCCACTGCTCCGACAAGCTATCGAGCTCTTCGATCACCAAGGTGCAGAGC 550
    ||||||||||||||||||||||||||||||||||||||||||||||||||
501 gccactgctccgacaagctatcgagctcttcgatcaccaaggtgcagagc 550

551 CAGCCTTCCTGTTCGGCCTTGAATTGATCATATGCGGATTGGAGAAGCAG 600
    ||||||||||||||||||||||||||||||||||||||||||||||||||
551 cagccttcctgttcggccttgaattgatcatatgcggattggagaagcag 600

601 CTGAAGTGTGAAAGTGGGTCTTAA 624
    ||||||||||||||||||||||||
601 ctgaagtgtgaaagtgggtcttaa 624
```

B. TetRMOD1 × TetRMOD3 (SEQ ID NO: 3 × SEQ ID NO: 5)

| | | | |
|---|---|---|---|
| Quality: | 6180 | Length: | 624 |
| Ratio: | 9.904 | Gaps: | 0 |
| Percent Similarity: | 99.038 | Percent Identity: | 99.038 |

```
  1 ATGTCTAGACTCGACAAGAGCAAGGTGATCAACAGCGCACTCGAGCTGCT 50
    |||| |||||||||||||||||||||||||||||||||||||||||||||
  1 ATGGCCAGACTCGACAAGAGCAAGGTGATCAACAGCGCACTCGAGCTGCT 50

51 GAACGAGGTCGGAATCGAAGGCCTCACAACCCGTAAACTCGCCCAGAAGC 100
    ||||||||||||||||||||||||||||||||||||||||||||||||||
 51 GAACGAGGTCGGAATCGAAGGCCTCACAACCCGTAAACTCGCCCAGAAGC 100

101 TCGGTGTAGAGCAGCCTACATTGTATTGGCATGTCAAGAACAAGCGGGCT 150
    |||| |||||||||||||||||||||||||||||||||||||||||||||
101 TCGGGGTAGAGCAGCCTACATTGTATTGGCATGTCAAGAACAAGCGGGCT 150
```

TABLE 8-continued

```
151 TTGCTCGACGCCCTCGCCATTGAGATGCTCGATAGGCACCATACCCACTT 200
    ||||||||||||||||||||||||||||||||||||||||||||||||||
151 TTGCTCGACGCCCTCGCCATTGAGATGCTCGATAGGCACCATACCCACTT 200

201 CTGCCCTTTGGAAGGGGAAAGCTGGCAAGACTTCCTGCGCAACAAGCGTA 250
    ||||||||||||||||||||||||||||||||||||||||||||||||||
201 CTGCCCTTTGGAAGGGGAAAGCTGGCAAGACTTCCTGCGCAACAACGCTA 250

251 AGAGCTTCAGATGTGCTTTGCTCAGTCATCGCGATGGAGCCAAGGTCCAC 300
    ||||||||||||||||||||||||||||||||||||||||||||||||||
251 AGAGCTTCAGATGTGCTTTGCTCAGTCATCGCGATGGAGCCAAGGTCCAC 300

301 TTGGGTACACGGCCTACAGAGAAGCAGTATGAAACTCTCGAGAACCAGCT 350
    ||||||||||||||||||||||||||||||||||||||||||||||||||
301 TTGGGTACACGGCCTACGGAGAAGCAGTATGAAACTCTCGAGAACCAGCT 350

351 CGCCTTCCTGTGCCAACAAGGTTTCTCCCTTGAGAATGCCCTCTACGCAC 400
    ||||||||||||||||||||||||||||||||||||||||||||||||||
351 CGCCTTCCTGTGCCAACAAGGTTTCTCCCTTGAGAATGCCCTCTACGCAC 400

401 TCAGCGCTGTGGGGCACTTCACTCTGGGTTGCGTATTGGAAGATCAAGAG 450
    ||  ||||||||||||||||||||||||||||||||||||||||||||||
401 TCTCCGCTGTGGGGCACTTCACTCTGGGTTGCGTATTGGAAGATCAAGAG 450

451 CATCAAGTCGCTAAGGAGGAGAGGGAAACACCTACTACTGATAGTATGCC 500
    ||||||||||||||||||||||||||||||||||||||||||||||||||
451 CATCAAGTCGCTAAGGAGGAGAGGGAAACACCTACTACTGATAGTATGCC 500

501 GCCACTGCTCCGACAAGCTATCGAGCTCTTCGATCACCAAGGTGCAGAGC 550
    ||||||||||||||||||||||||||||||||||||||||||||||||||
501 GCCACTGCTCCGACAAGCTATCGAGCTCTTCGATCACCAAGGTGCAGAGC 550

551 CAGCCTTCCTGTTCGGCCTTGAATTGATCATATGCGGATTGGAGAAGCAG 600
    ||||||||||||||||||||||||||||||||||||||||||||||||||
551 CAGCCTTCCTGTTCGGCCTTGAATTGATCATATGCGGATTGGAGAAGCAG 600

601 CTGAAGTGTGAAAGTGGGTCTTAA 624
    ||||||||||||||||||||||||
601 CTGAAGTGTGAAAGTGGGTCTTAA 624
```

C. TetRMOD1 × TetRMOD4    (SEQ ID NO: 3 × SEQ ID NO: 11)

| | | | |
|---|---|---|---|
| Quality: | 6060 | Length: | 624 |
| Ratio: | 9.712 | Gaps: | 0 |
| Percent Similarity: | 97.115 | Percent Identity: | 97.115 |

```
  1 ATGTCTAGACTCGACAAGAGCAAGGTGATCAACAGCGCACTCGAGCTGCT 50
    |||  |||||||||||||||||||||||||||||||||||||||||||||
  1 arggccagactcgacaagagcaaggtgatcaacagcgcactggagctgct 50

51 GAACGAGGTCGGAATCGAAGGCCTCACAACCCGTAAACTCGCCCAGAAGC 100
    ||||||||||||||||||||||||||||||||||||||||||||||||||
 51 gaacgaggtcggaatcgaaggcctcacaacccgtaaactcgcccagaagc 100

101 TCGGTGTAGAGCAGCCTACATTGTATTGGCATGTCAAGAACAAGCGGGCT 150
    ||||  ||||||||||||||||||||||||| ||||||||||||||||||
101 tcggggtagagcagcctacattgtattggcacgtcaagaacaagcgggct 150

151 TTGCTCGACGCCCTCGCCATTGAGATGCTCGATAGGCACCATACCCACTT 200
    ||||| ||||||||||||||||||||||||||||||||||||||||||||
151 ttgctagacgccctcgccattgagatgctcgataggcaccatacccactt 200

201 CTGCCCTTTGGAAGGGGAAAGCTGGCAAGACTTCCTGCGCAACAAGCGTA 250
    ||||||||||||||||||||||||||||||||||||| || ||||||||| 
201 ctgccctttggaaggggaaagctggcaagacttcttgaggaacaacgcta 250

251 AGAGCTTCAGATGTGCTTTGCTCAGTCATCGCGATGGAGCCAAGGTCCAC 300
    |||| |||||||||||||||||||||||| || |||||||||||||||||
251 agaacttcagatgtgctttgctcagtcaccgtgatggagccaaggtccac 300

301 TTGGGTACACGGCCTACAGAGAAGCAGTATGAAACTCTCGAGAACCAGCT 350
    | ||||||||||||||| ||||||||||||||||||||||||||||||||
301 ctaggtacacggcctacggagaagcagtatgaaactctcgagaaccagct 350
```

TABLE 8-continued

```
351 CGCCTTCCTGTGCCAACAAGGTTTCTCCCTTGAGAATGCCCTCTACGCAC 400
    ||||||||||||||||||||||||||||||||||||||||||||||||||
351 cgccttcctgtgccaacaaggtttctcccttgagaatgccctctacgcac 400

401 TCAGCGCTGTGGGGCACTTCACTCTGGGTTGCGTATTGGAAGATCAAGAG 450
    ||  ||||||  ||||||||||||||||||||||||||||||||||||||
401 tctccgctgtagggcacttcactctgggttgcgtattggaagatcaagag 450

451 CATCAAGTCGCTAAGGAGGAGAGGGAAACACCTACTACTGATAGTATGCC 500
    ||  ||||||||||||||||||||||||||||||||||||||||||||||
451 caccaagtcgctaaggaggagagggaaacacctactactgatagtatgcc 500

501 GCCACTGCTCCGACAAGCTATCGAGCTCTTCGATCACCAAGGTGCAGAGC 550
    ||||||||||||||||||||||||||||||||||||||||||||||||||
501 gccactgctccgacaagctatcgagctcttcgatcaccaaggtgcagagc 550

551 CAGCCTTCCTGTTCGGCCTTGAATTGATCATATGCGGATTGGAGAAGCAG 600
    ||||||||||||||||||||||||||||||||||||||||||||||||||
551 cagccttcctgttcggccttgaattgatcatatgcggattggagaagcag 600

601 CTGAAGTGTGAAAGTGGGTCTTAA 624
    ||||||||||||||||||||||||
601 ctgaagtgtgaaagtgggtcttaa 624
```

D. TetRMOD1 x TetR (GI43051) (SEQ ID NO: 3 x SEQ ID NO: 1)

```
  1 ATGTCTAGACTCGACAAGAGCAAGGTGATCAACAGCGCACTCGAGCTGCT 50
    |||||||||  |  ||  ||  ||  |||||  |||||||||  ||||||||
  1 ATGTCTAGATTAGATAAAAGTAAAGTGATTAACAGCGCATTAGAGCTGCT 50

51 GAACGAGGTCGGAATCGAAGGCCTCACAACCCGTAAACTCGCCCAGAAGC 100
    ||  ||||||||||||||||||  ||  ||||||||||||||||||||||
 51 TAATGAGGTCGGAATCGAAGGTTTAACAACCCGTAAACTCGCCCAGAAGC 100

101 TCGGTGTAGAGCAGCCTACATTGTATTGGCATGTCAAGAACAAGCGGGCT 150
    |  |||||||||||||||||||||||||||||||  ||  ||||||||||
101 TAGGTGTAGAGCAGCCTACATTGTATTGGCATGTAAAAAATAAGCGGGCT 150

151 TTGCTCGACGCCCTCGCCATTGAGATGCTCGATAGGCACCATACCCACTT 200
    |||||||||  ||  |||||||||||||||  ||||||||||||| ||||
151 TTGCTCGACGCCTTAGCCATTGAGATGTTAGATAGGCACCATACTCACTT 200

201 CTGCCCTTTGGAAGGGGAAAGCTGGCAAGACTTCCTGCGCAACAAGCGTA 250
    ||||||||  ||||||||||||||||||||  ||  |  ||  ||||||  
201 TTGCCCTTTAGAAGGGGAAAGCTGGCAAGATTTTTTACGTAATAACGCTA 250

251 AGAGCTTCAGATGTGCTTTGCTCAGTCATCGCGATGGAGCCAAGGTCCAC 300
    |  ||  ||||||||||||  ||  |||||||||||||||||  ||  ||
251 AAAGTTTTAGATGTGCTTTACTAAGTCATCGCGATGGAGCAAAAGTACAT 300

301 TTGGGTACACGGCCTACAGAGAAGCAGTATGAAACTCTCGAGAACCAGCT 350
    || ||||||||||||||||  ||  ||||||||||||||||  ||  |  |
301 TTAGGTACACGGCCTACAGAAAAACAGTATGAAACTCTCGAAAATCAATT 350

351 CGCCTTCCTGTGCCAACAAGGTTTCTCCCTTGAGAATGCCCTCTACGCAC 400
    |||||  |  ||||||||||||||  ||  ||||||||  |  || ||||
351 AGCCTTTTTATGCCAACAAGGTTTTTCACTAGAGAATGCATTATATGCAC 400

401 TCAGCGCTGTGGGGCACTTCACTCTGGGTTGCGTATTGGAAGATCAAGAG 450
    |||||||||||||||  ||  |||  |||||||||||||||||||||||
401 TCAGCGCTGTGGGGCATTTTACTTTAGGTTGCGTATTGGAAGATCAAGAG 450

451 CATCAAGTCGCTAAGGAGGAGAGGGAAACACCTACTACTGATAGTATGCC 500
    |||||||||||||  ||  |||||||||||||||||||||||||||||||
451 CATCAAGTCGCTAAAGAAGAAAGGGAAACACCTACTACTGATAGTATGCC 500

501 GCCACTGCTCCGACAAGCTATCGAGCTCTTCGATCACCAAGGTGCAGAGC 550
    ||||  |  |  ||||||||||||||  |||  |||||||||||||||||
501 GCCATTATTACGACAAGCTATCGAATTATTTGATCACCAAGGTGCAGAGC 550

551 CAGCCTTCCTGTTCGGCCTTGAATTGATCATATGCGGATTGGAGAAGCAG 600
    |||||||||  ||||||||||||||||||||||||||||||  ||  ||
551 CAGCCTTCTTATTCGGCCTTGAATTCATCATATGCGGATTAGAAAAACAA 600

601 CTGAAGTGTGAAAGTGGGTCTTAA 624
    ||  || ||||||||||||||||||
601 CTTAAATGTGAAAGTGGGTCTTAA 624
```

TABLE 8-continued

E. TetRMOD2 x TetRMOD3 (SEQ ID NO: 13 x SEQ ID NO: 5)

Quality:           6120      Length:              624
Ratio:             9.808     Gaps:                0
Percent Similarity: 98.077   Percent Identity:    98.077

```
  1 atgtctagactcgacaagagcaaggtgatcaacagcgcactcgagctgct 50
    ||| | ||||||||||||||||||||||||||||||||||||||||||||
  1 ATGGCCAGACTCGACAAGAGCAAGGTGATCAACAGCGCACTCGAGCTGCT 50

51 gaacgaggtcggaatcgaaggcctcacaacccgtaaactcgcccagaagc 100
    ||||||||||||||||||||||||||||||||||||||||||||||||||
 51 GAACGAGGTCGGAATCGAAGGCCTCACAACCCGTAAACTCGCCCAGAAGC 100

101 tcggtgtagagcagcctacattgtattggcacgtcaagaacaagcgggct 150
    |||| |||||||||||||||||||||||| ||||||||||||||||||||
101 TCGGGGTAGAGCAGCCTACATTGTATTGGCATGTCAAGAACAAGCGGGCT 150

151 ttgctagacgccctcgccattgagatgctcgataggcaccatacccactt 200
    ||||| |||||||||||||||||||||||| |||||||||||||||||||
151 TTGCTCGACGCCCTCGCCATTGAGATGCTCGATAGGCACCATACCCACTT 200

201 ctgccctttggaaggggaaagctggcaagacttcttgaggaacaacgcta 250
    |||||||||||||||||||||||||||||||||| |||||||||||||||
201 CTGCCCTTTGGAAGGGGAAAGCTGGCAAGACTTCCTGCGCAACAACGCTA 250

251 agagcttcagatgtgctttgctcagtcatcgcgatggagccaaggtccac 300
    ||||||||||||||||||||||||||||||||||||||||||||||||||
251 AGAGCTTCAGATGTGCTTTGCTCAGTCATCGCGATGGAGCCAAGGTCCAC 300

301 ttgggtacacggcctacagagaagcagtatgaaactctcgagaaccagct 350
    ||||||||||||||||||||||||||||||||||||||||||||||||||
301 TTGGGTACACGGCCTACGGAGAAGCAGTATGAAACTCTCGAGAACCAGCT 350
```

F. TetRMOD2 x TetRMOD4 (SEQ ID NO: 13 x SEQ ID NO: 11)

Quality:           6120      Length:              624
Ratio:             9.808     Gaps:                0
Percent Similarity: 98.077   Percent Identity:    98.077

```
  1 atgtctagactcgacaagagcaaggtgatcaacagcgcactcgagctgct 50
    ||| | ||||||||||||||||||||||||||||||||||||||||||||
  1 atggccagactcgacaagagcaaggtgatcaacagcgcactggagctgct 50

51 gaacgaggtcggaatcgaaggcctcacaacccgtaaactcgcccagaagc 100
    ||||||||||||||||||||||||||||||||||||||||||||||||||
 51 gaacgaggtcggaatcgaaggcctcacaacccgtaaactcgcccagaagc 100

101 tcggtgtagagcagcctacattgtattggcacgtcaagaacaagcgggct 150
    |||| |||||||||||||||||||||||||||||||||||||||||||||
101 tcggggtagagcagcctacattgtattggcacgtcaagaacaagcgggct 150

151 ttgctagacgccctcgccattgagatgctcgataggcaccatacccactt 200
    ||||||||||||||||||||||||||||||||||||||||||||||||||
151 ttgctagacgccctcgccattgagatgctcgataggcaccatacccactt 200

201 ctgccctttggaaggggaaagctggcaagacttcttgaggaacaacgcta 250
    ||||||||||||||||||||||||||||||||||||||||||||||||||
201 ctgccctttggaaggggaaagctggcaagacttcttgaggaacaacgcta 250

251 agagcttcagatgtgctttgctcagtcatcgcgatggagccaaggtccac 300
    |||||||||||||||||||||||||||| |||||||||||||||||||||
251 agagcttcagatgtgctttgctcagtcaccgtgatggagccaaggtccac 300

301 ttgggtacacggcctacagagaagcagtatgaaactctcgagaaccagct 350
    || ||||||||||||||| |||||||||||||||||||||||||||||||
301 ctaggtacacggcctacggagaagcagtatgaaactctcgagaaccagct 350

351 cgccttcctgtgccaacaaggtttctcccttgagaatgccctctacgcac 400
    ||||||||||||||||||||||||||||||||||||||||||||||||||
351 cgccttcctgtgccaacaaggtttctcccttgagaatgccctctacgcac 400

401 tcagcgctgtagggcacttcactctgggttgcgtattggaagatcaagag 450
    || |||||||||||||||||||||||||||||||||||||||||||||||
401 tctccgctgtagggcacttcactctgggttgcgtattggaagatcaagag 450
```

TABLE 8-continued

```
451 catcaagtcgctaaggaggagagggaaacacctactactgatagtatgcc 500
    ||  |||||||||||||||||||||||||||||||||||||||||||||
451 caccaagtcgctaaggaggagagggaaacacctactactgatagtatgcc 500

501 gccactgctccgacaagctatcgagctcttcgatcaccaaggtgcagagc 550
    ||||||||||||||||||||||||||||||||||||||||||||||||||
501 gccactgctccgacaagctatcgagctcttcgatcaccaaggtgcagagc 550

551 cagccttcctgttcggccttgaattgatcatatgcggattggagaagcag 600
    ||||||||||||||||||||||||||||||||||||||||||||||||||
551 cagccttcctgttcggccttgaattgatcatatgcggattggagaagcag 600

601 ctgaagtgtgaaagtgggtcttaa 624
    ||||||||||||||||||||||||
601 ctgaagtgtgaaagtgggtcttaa 624
```

G. TetRMOD2 x TetR (GI43051) (SEQ ID NO: 13 x SEQ ID NO: 1)

| | | | |
|---|---|---|---|
| Quality: | 5400 | Length: | 624 |
| Ratio: | 8.654 | Gaps: | 0 |
| Percent Similarity: | 86.538 | Percent Identity: | 86.538 |

```
  1 atgtctagactcgacaagagcaaggtgatcaacagcgcactcgagctgct 50
    ||||||||| |  ||  || ||  |||| ||||||||   |  |||||||
  1 ATGTCTAGATTAGATAAAAGTAAAGTGATTAACAGCGCATTAGAGCTGCT 50

51 gaacgaggtcggaatcgaaggcctcacaacccgtaaactcgcccagaagc 100
    || |||||||||||||||||||  ||||  ||||||||||||||||||||
 51 TAATGAGGTCGGAATCGAAGGTTTAACAACCCGTAAACTCGCCCAGAAGC 100

101 tcggtgtagagcagcctacattgtattggcacgtcaagaacaagcgggct 150
    |  ||||||||||||||||||||||||||| ||| ||  || ||||||||
101 TAGGTGTAGAGCAGCCTACATTGTATTGGCATGTAAAAAATAAGCGGGCT 150

151 ttgctagacgccctcgccattgagatgctcgataggcaccatacccactt 200
    |||||  ||||||||| |||||||||||| ||||||||||||| |||||
151 TTGCTCGACGCCCTTAGCCATTGAGATGTTAGATAGGCACCATACTCACTT 200

201 ctgcccttggaaggggaaagctggcaagacttcttgaggaacaacgcta 250
    ||||||||| |||||||||||||||||||| ||||| |||||||||||||
201 TTGCCCTTTAGAAGGGGAAAGCTGGCAAGATTTTTTACGTAATAACGCTA 250

251 agagcttcagatgtgctttgctcagtcatcgcgatggagccaaggtccac 300
    | || || |||||||||||| || |||||||||||||||||  || || ||
251 AAAGTTTTAGATGTGCTTTACTAAGTCATCGCGATGGAGCAAAAGTACAT 300

301 ttgggtacacggcctacagagaagcagtatgaaactctcgagaaccagct 350
    || |||||||||||||||| || ||||||||||||||||||  || || |
301 TTAGGTACACGGCCTACAGAAAAACAGTATGAAACTCTCGAAAATCAATT 350

351 cgccttcctgtgccaacaaggtttctcccttgagaatgccctctacgcac 400
    |||||    | |||||||||||||| ||  || |||||||   |  ||||
351 AGCCTTTTTATGCCAACAAGGTTTTTCACTAGAGAATGCATTATATGCAC 400

401 tcagcgctgtagggcacttcactctgggttgcgtattggaagatcaagag 450
    ||||||||||| |||||||| |  || |||||||||||||||||||||||
401 TCAGCGCTGTGGGGCATTTTACTTTAGGTTGCGTATTGGAAGATCAAGAG 450

451 catcaagtcgctaaggaggagagggaaacacctactactgatagtatgcc 500
    ||||||||||||||  ||  || ||||||||||||||||||||||||||
451 CATCAAGTCGCTAAAGAAGAAAGGGAAACACCTACTACTGATAGTATGCC 500

501 gccactgctccgacaagctatcgagctcttcgatcaccaaggtgcagagc 550
    |||| |  |||||||||||||| |  || ||||||||||||||||||||
501 GCCATTATTACGACAAGCTATCGAATTATTTGATCACCAAGGTGCAGAGC 550

551 cagccttcctgttcggccttgaattgatcatatgcggattggagaagcag 600
    |||||||| | |||||||||||||||||||||||||||||| ||   ||
551 CAGCCTTCTTATTCGGCCTTGAATTGATCATATGCGGATTAGAAAAACAA 600

601 ctgaagtgtgaaagtgggtcttaa 624
    || || ||||||||||||||||||
601 CTTAAATGTGAAAGTGGGTCTTAA 624
```

TABLE 8-continued

H. TetRMOD3 x TetRMOD4 (SEQ ID NO: 5 x SEQ ID NO: 11)

Quality:           6120      Length:                 624
Ratio:             9.808     Gaps:                     0
Percent Similarity: 98.077   Percent Identity:    98.077

```
  1 atgtctagactcgacaagagcaaggtgatcaacagcgcactcgagctgct 50
    ||| | ||||||||||||||||||||||||||||||||||| ||||||||
  1 atggccagactcgacaagagcaaggtgatcaacagcgcactggagctgct 50

51 gaacgaggtcggaatcgaaggcctcacaacccgtaaactcgcccagaagc 100
    ||||||||||||||||||||||||||||||||||||||||||||||||||
 51 gaacgaggtcggaatcgaaggcctcacaacccgtaaactcgcccagaagc 100

101 tcggtgtagagcagcctacattgtattggcacgtcaagaacaagcgggct 150
    ||||  ||||||||||||||||||||||||||||||||||||||||||||
101 tcggggtagagcagcctacattgtattggcacgtcaagaacaagcgggct 150

151 ttgctagacgccctcgccattgagatgctcgataggcaccatacccactt 200
    ||||||||||||||||||||||||||||||||||||||||||||||||||
151 ttgctagacgccctcgccattgagatgctcgataggcaccatacccactt 200

201 ctgcccttggaaggggaaagctggcaagacttcttgaggaacaacgcta 250
    ||||||||||||||||||||||||||||||||||||||||||||||||||
201 ctgcccttggaaggggaaagctggcaagacttcttgaggaacaacgcta 250

251 agagcttcagatgtgctttgctcagtcatcgcgatggagccaaggtccac 300
    |||||||||||||||||||||||||||| | |||||||||||||||||||
251 agagcttcagatgtgctttgctcagtcaccgtgatggagccaaggtccac 300

301 ttgggtacacggcctacagagaagcagtatgaaactctcgagaaccagct 350
    || |||||||||||||||||  ||||||||||||||||||||||||||||
301 ctaggtacacggcctacggagaagcagtatgaaactctcgagaaccagct 350

351 CGCCTTCCTGTGCCAACAAGGTTTCTCCCTTGAGAATGCCCTCTACGCAC 400
    ||||||||||||||||||||||||||||||||||||||||||||||||||
351 cgccttcctgtgccaacaaggtttctcccttgagaatgccctctacgcac 400

401 TCTCCGCTGTGGGGCACTTCACTCTGGGTTGCGTATTGGAAGATCAAGAG 450
    ||||||||||| |||||||||||||||||||||||||||||||||||||
401 tctccgctgtagggcacttcactctgggttgcgtattggaagatcaagag 450

451 CATCAAGTCGCTAAGGAGGAGAGGGAAACACCTACTACTGATAGTATGCC 500
    || |||||||||||||||||||||||||||||||||||||||||||||||
451 caccaagtcgctaaggaggagagggaaacacctactactgatagtatgcc 500

501 GCCACTGCTCCGACAAGCTATCGAGCTCTTCGATCACCAAGGTGCAGAGC 550
    ||||||||||||||||||||||||||||||||||||||||||||||||||
501 gccactgctccgacaagctatcgagctcttcgatcaccaaggtgcagagc 550

551 CAGCCTTCCTGTTCGGCCTTGAATTGATCATATGCGGATTGGAGAAGCAG 600
    ||||||||||||||||||||||||||||||||||||||||||||||||||
551 cagccttcctgttcggccttgaattgatcatatgcggattggagaagcag 600

601 CTGAAGTGTGAAAGTGGGTCTTAA 624
    ||||||||||||||||||||||||
601 ctgaagtgtgaaagtgggtcttaa 624
```

I. TetRMOD3 x TetR (GI43051) (SEQ ID NO: 5 x SEQ ID NO: 1)

Quality:           5370      Length:                 624
Ratio:             8.606     Gaps:                     0
Percent Similarity: 86.058   Percent Identity:    86.058

```
  1 ATGGCCAGACTCGACAAGAGCAAGGTGATCAACAGCGCACTCGAGCTGCT 50
    ||| | ||| || || || ||||| |||||||||||||||| ||||||||
  1 ATGTCTAGATTAGATAAAAGTAAAGTGATTAACAGCGCATTAGAGCTGCT 50

51 GAACGAGGTCGGAATCGAAGGCCTCACAACCCGTAAACTCGCCCAGAAGC 100
    || |||||||||||||||||| ||  ||||||||||||||||||||||||
 51 TAATGAGGTCGGAATCGAAGGTTTAACAACCCGTAAACTCGCCCAGAAGC 100

101 TCGGGGTAGAGCAGCCTACATTGTATTGGCATGTCAAGAACAAGCGGGCT 150
    |  || ||||||||||||||||||||||||||||||||  ||  ||||||
101 TAGGTGTAGAGCAGCCTACATTGTATTGGCATGTAAAAAATAAGCGGGCT 150
```

TABLE 8-continued

```
151 TTGCTCGACGCCCTCGCCATTGAGATGCTCGATAGGCACCATACCCACTT 200
    |||||||||| | |||||||||||| | ||||||||||||||||| |||||
151 TTGCTCGACGCCTTAGCCATTGAGATGTTAGATAGGCACCATACTCACTT 200

201 CTGCCCTTTGGAAGGGGAAAGCTGGCAAGACTTCCTGCGCAACAAGCGTA 250
    |||||||| ||||||||||||||||||| || | || || ||||||
201 TTGCCCTTTAGAAGGGGAAAGCTGGCAAGATTTTTTACGTAATAACGCTA 250

251 AGAGCTTCAGATGTGCTTTGCTCAGTCATCGCGATGGAGCCAAGGTCCAC 300
    | || || |||||||||||| || |||||||||||||||| || || ||
251 AAAGTTTTAGATGTGCTTTACTAAGTCATCGCGATGGAGCAAAAGTACAT 300

301 TTGGGTACACGGCCTACGGAGAAGCAGTATGAAACTCTCGAGAACCAGCT 350
    || |||||||||||||| || || ||||||||||||||||| || || |
301 TTAGGTACACGGCCTACAGAAAAACAGTATGAAACTCTCGAAAATCAATT 350

351 CGCCTTCCTGTGCCAACAAGGTTTCTCCCTTGAGAATGCCCTCTACGCAC 400
    ||||| | ||||||||||||||| || || |||||||| | || ||||
351 AGCCTTTTTATGCCAACAAGGTTTTTCACTAGAGAATGCATTATATGCAC 400

401 TCTCCGCTGTGGGGCACTTCACTCTGGGTTGCGTATTGGAACATCAAGAG 450
    || |||||||||| || ||| | |||||||||||||| ||||||||||
401 TCAGCGCTGTGGGGCATTTTACTTTAGGTTGCGTATTGGAAGATCAAGAG 450

451 CATCAAGTCGCTAAGGAGGAGAGGGAAACACCTACTACTGATAGTATGCC 500
    |||||||||||||| || || ||||||||||||||||||||||||||||
451 CATCAAGTCGCTAAAGAAGAAAGGGAAACACCTACTACTGATAGTATGCC 500

501 GCCACTGCTCCGACAAGCTATCGAGCTCTTCGATCACCAAGGTGCAGAGC 550
    |||| | | |||||||||||| ||| || || ||||||||||||||||||
501 GCCATTATTACGACAAGCTATCGAATTATTTGATCACCAAGGTGCAGAGC 550

551 CAGCCTTCCTGTTCGGCCTTGAATTGATCATATGCGGATTGGAGAAGCAG 600
    |||||||| | |||||||||||||||||||||||||||||||| || || ||
551 CAGCCTTCTTATTCGGCCTTGAATTCATCATATGCGGATTAGAAAAACAA 600

601 CTGAAGTGTGAAAGTGGGTCTTAA 624
    || || ||||||||||||||||||
601 CTTAAATGTGAAAGTGGGTCTTAA 624
```

J. TetRMOD4 x TetR (GI43051) (SEQ ID NO: 11 x SEQ ID NO: 1)

Quality:           5310      Length:               624
Ratio:             8.510     Gaps:                   0
Percent Similarity: 85.096   Percent Identity:   85.096

```
  1 atggccagactcgacaagagcaaggtgatcaacagcgcactggagctgct 50
    ||| | ||| || || || || || ||||| |||||||||| | ||||||||
  1 ATGTCTAGATTAGATAAAAGTAAAGTGATTAACAGCGCATTAGAGCTGCT 50

51 gaacgaggtcggaatcgaaggcctcacaacccgtaaactcgcccagaagc 100
    || |||||||||||||||||||  | ||||||||||||||||||||||||
 51 TAATGAGGTCGGAATCGAAGGTTTAACAACCCGTAAACTCGCCCAGAAGC 100

101 tcggggtagagcagcctacattgtattggcacgtcaagaacaagcgggct 150
    | || |||||||||||||||||||||||| || || |||||||||||||
101 TAGGTGTAGAGCAGCCTACATTGTATTGGCATGTAAAAAATAAGCGGGCT 150

151 ttgctagacgccctcgccattgagatgctcgataggcaccatacccactt 200
    ||||| ||||||| |||||||||||||| |||||||||||||| |||||
151 TTGCTCGACGCCTTAGCCATTGAGATGTTAGATAGGCACCATACTCACTT 200

201 ctgcccttt ggaaggggaaagctggcaagacttcttgaggaacaacgcta 250
    ||||||||| ||||||||||||||||||||| || || || || ||||
201 TTGCCCTTTAGAAGGGGAAAGCTGGCAAGATTTTTTACGTAATAACGCTA 250

251 agagcttcagatgtgctttgctcagtcaccgtgatggagccaaggtccac 300
    | || || ||||||||||| || ||||| ||||||||| || || ||
251 AAAGTTTTAGATGTGCTTTACTAAGTCATCGCGATGGAGCAAAAGTACAT 300

301 ctaggtacacggcctacgagaagcagtatgaaactctcgagaaccagct 350
    ||||||||||||||| || || |||||||||||||||||| || || |
301 TTAGGTACACGGCCTACAGAAAAACAGTATGAAACTCTCGAAAATCAATT 350
```

Example 2

Promoters Regulatable by TetR

Promoters and methods to produce promoters modified to be regulated by tetracycline and analogs thereof by introduction of one or more TetOp sequences are known (Matzke, et al., (2003) *Plant Mol Biol Rep* 21:9-19; Padidam (2003) *Curr Op Plant Biol* 6:169-177; Gatz and Quail (1988) *Proc Natl Acad Sci USA* 85:1394-1397; Ulmasov, et al., (1997) *Plant Mol Biol* 35:417-424). Any promoter functional in the host cell can be modified and tested using standard techniques and assays.

CaMV 35S pro-3XopT

The CaMV 35S 3XopT (Triple-Op) promoter essentially as described by Gatz, et al., (Plant J 2:397-404 1992) was used for vector construction. The promoter element used comprises CaMV 35S promoter with the TATA box flanked by three tet operator sequences. The 19 bp hybrid TetOp sequence used is shown in SEQ ID NO: 10. The operators are arranged so that one TetOp sequence is 5' to the TATA box and 2 TetOp sequences are 3' to the TATA box. The entire 656 bp promoter cassette with flanking sequence and restriction enzyme sites is:

NcoI(2)-SmaI(101)-XhoI(105)-CaMV35S-EcoRV(450)::TetOp1::TATA::TetOp1::TetOp1::Ω' 5'UTR-SalI(631)-BglII(638)

Example 3

Vector Construction

Vectors can be constructed using standard molecular biology techniques. The following vectors were generated using standard techniques to assemble the components, which were optionally inserted into a T-DNA vector system. The symbol "::" indicates operably linked components which form a functional unit.

A. Inducible Visual Marker

T-DNA vector PHP24683 comprises:
LB-35S pro-3XOpT::Ω' 5'UTR::Adh1 intron::DsRED2::pinII term-ubi pro::moTetR::pinII term-ubi pro::moPAT::pinII-RB B. Inducible ODP2

T-DNA vector PHP25-1 comprises:
LB-35S pro-3XOpT::Ω' 5'UTR::Adh1 intron::ODP2-pinII term-ubi pro::ubi intron::moT etR::pinII term-ubi pro::ubi intron::m oPAT::pinII-RB wherein moTe tR is TetRMO D4 (SEQ ID NO:11).

Example 4

Transformation

Transient and/or stable transformation of any plant, plant cell, and/or plant tissue can be done using any one of the suitable standard protocols available including direct delivery methods, such as particle gun methods, and other delivery methods, such as *Agrobacterium*-mediated methods.

*Agrobacterium*-mediated Delivery

Immature embryos, typically about 1.0-1.5 mm, from Hi-II or maize inbred lines were transformed with *Agrobacterium* comprising a T-DNA vector using an *Agrobacterium*-mediated method essentially as described in U.S. Pat. No. 5,981,840. *Agrobacteria* containing the T-DNA(s) were grown to the log phase in liquid minimal medium containing 100 µM spectinomycin. Embryos were immersed in a log phase suspension of *Agrobacteria* adjusted to an effective concentration of $5 \times 10^8$ cfu/ml. Embryos were infected 5 minutes, then co-cultured in the dark for 7 days at 20° C. on medium containing acetosyringone. After 7 days, the embryos were transferred to standard culture medium with 3 mg/L Bialaphos®. Plates were maintained at 28° C. in the dark and were observed for colony recovery with transfers to fresh medium every two to three weeks. Bialaphos® resistant colonies and regenerated plants were recovered and used for various analyses and characterizations described below.

Example 5

Regulating Expression of a Polynucleotide of Interest

A. Inducible Expression of DsRED Visual Marker

Maize Hi-II was transformed with PHP24683 essentially as described in Example 4. One to two days after transformation, transient expression of DsRED was observed, indicating successful DNA delivery into scutellar cells. The initial transient expression in the absence of inducer gradually disappeared during continued culture. After 8 weeks on selective medium containing 3 mg/L Bialaphos®, callus events exhibited no red fluorescence in the absence of tetracycline, indicating tight regulation by tetracycline repressor. When vigorously growing callus was subcultured onto medium containing 12.5 mg/L tetracycline, red fluorescence was observed after 24 hours using an Nikon epifluorescent stereomicroscope which has a bandpass filter that permits the excitation wavelengths between 515-575 nm to pass through. Chlorophylls absorb very strongly below 450 nm, but absorb very little between 500-575 nm, therefore using this filter chlorophyll background autofluorescence is very low and does not interfere with the detection of RFP expression.

A fluorometric quantitative assay was used to analyze protein extracts from non-transgenic control callus, and 10 bialaphos-resistant calli treated with tetracycline for various timepoints. DsRED2 protein expressed in maize was purified and used to generate the standard curve for the fluorometric assay (DsRed2 protein is property of BD Biosciences Clontech, Bedford, Mass.). The protein extract from non-transgenic control callus exhibited no fluorescence under any treatment. Protein extracts from the 10 transgenic events showed no background red fluorescence in the absence of ligand. Upon exposure to 12.5 mg/L tetracycline, 9/10 events exhibited red fluorescence which generally increased with longer exposure to the ligand (see, Table 7).

TABLE 7

| Event ID | ng DsRED/mg total protein | | | |
|---|---|---|---|---|
| | 0 hr | 24 hr | 48 hr | 72 hr |
| 489 | 0 | 0.32 | 1.36 | 1.03 |
| 490 | 0 | 0.23 | 0.70 | 0.98 |
| 491 | 0 | 0.13 | 0.50 | 0.57 |
| 492 | 0 | 0.12 | 0.41 | 0.24 |
| 493 | 0 | 0 | 0.23 | 0 |
| 494 | 0 | 0.24 | 0.63 | 0.77 |
| 495 | 0 | 0 | 0 | 0.29 |
| 497 | 0 | 0 | 0.35 | 0.80 |
| 503 | 0 | 0 | 0 | 0 |
| 517 | 0 | 0 | 0.23 | 0.76 |
| Negative Control | 0 | 0 | 0 | 0 |

Further events were generated by additional transformations with PHP24683. A total of 100 bialaphos-resistant events were recovered, and of these, 87 had no detectable leaky expression of DsRED in the absence of ligand, and showed inducible DsRED expression upon exposure to tetracycline. The remaining 13 failed to induce in the presence of the ligand.

Two inducer ligands, tetracycline and doxycycline, were tested. Microscopic evaluation detected red fluorescence using a tetracycline concentration as low as 0.1 mg/L, while for doxycycline red fluorescence was observed at 0.025 mg/L.

Plants were regenerated from 20 events and sent to the greenhouse. After exposing various plant parts to 1 mg/L tetracycline for 24 hours, strong red fluorescence was observed in all plant parts examined, including leaves, roots, stem, immature ear, silks, ovules, embryos, tassel, anthers and pollen.

A positive control callus event was identified based on previous comparison to purified tetracycline repressor standard (Mo Bi Tec, Göttingen, Germany) and used as an internal reference standard on the gel to normalize results from each event extract. Twenty milligrams each of tetracycline-treated and untreated callus from this event was extracted with 0.5 ml extraction buffer (136 mM NaCl, 8 mM $NaPO_4$, 1.5 mM KPO4, 2.7 mM KCl, 0.05% v/v Tween-20, pH 7.4). The supernatants both extracts were pooled and total protein concentration determined using Bradford assay (BioRad, Hercules, Calif., USA). The positive control extract was diluted to 0.5 mg/ml in gel sample buffer (50 mM Tris-HCl pH 7.5, 1% v/v SDS, 2% v/v β-mercaptoethanol, 0.02% w/v bromophenol blue, 10% v/v glycerol), and stored at −20° C. All gels were loaded with 20 µl positive callus extract comprising 10 µg total protein.

Callus extracts used for fluorometric quantification of DsRED were subjected to SDS-PAGE and western analysis using standard protocols with a commercially available monoclonal antibody to tetracycline repressor (Cat# TET02, Mo Bi Tec, Göttingen, Germany). For each protein extract, 18 µg total protein was loaded per lane of the gel. After gel transfer and blocking, the blot was probed with primary antibody diluted 1:8000 in 3% low fat milk/PBST and incubated overnight at 4° C. Blots were washed with PBST, then incubated with the HRP-labeled goat anti-mouse diluted 1:5000 (Promega Corp., Madison, Wis., USA). The blots were developed using an ECL™ detection kit (Amersham Biosciences Corp., Piscataway, N.J., USA) and exposed to film. The film bands were scanned using a densitometer to determine relative amount of TetR protein in test and control extracts. Non-transgenic control callus produced no signal (0% TetR), and all ten of the transformed events produced positive bands, with relative values shown in Table 8.

TABLE 8

| Event ID | Relative Amount TetR |
|---|---|
| 489 | 68% |
| 490 | 44% |
| 491 | 38% |
| 492 | 24% |
| 493 | 90% |
| 494 | 30% |
| 495 | 68% |
| 497 | 53% |
| 503 | 20% |
| 517 | 78% |
| Negative Control | 0% |

B. Tetracycline-inducible Expression of ODP2

ODP2 is a transcription factor normally expressed early in embryo development in maize. Many homologues are known from different plant species including but not limited to maize, rice, Brassica, and Arabidopsis. In maize, overexpression of ODP2 can stimulate somatic embryo formation and enhance recovery of transformants (US Publication Number 2005/0257289, herein incorporated by reference).

Immature maize embryos were transformed with PHP25271. After Agrobacterium-mediated transformation, events were cultured for 8 weeks on selection medium containing 3 mg/L bialaphos, transgenic events were regenerated, and plants sent to the greenhouse. All regenerated plants produced were normal, fertile, and produced viable mature seed.

Figure 2:
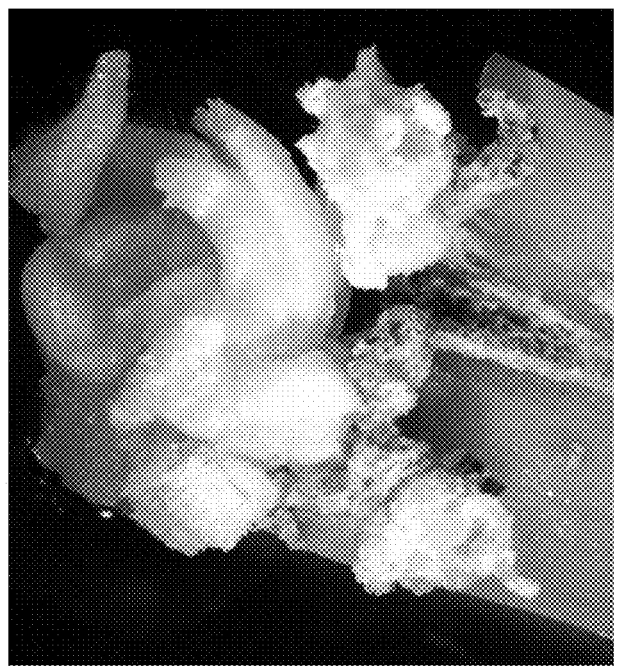
FIG. 2. Somatic embryo and shoot formation on cut edges of 1 cm leaf segments of transgenic maize TC-inducible ODP2 T2 plantlets placed on medium containing 1 mg/L doxycycline.

Selected progeny plantlets were cut into approximately 1 cm segments and placed on culture medium containing 1 mg/L doxycycline. Explants from these transgenic plantlets produced callus, while explants from non-transgenic controls did not produce callus (FIG. 1). Higher magnification micrographs reveal the formation of somatic embryos derived from leaf explants, and new shoots were beginning to develop from some of these somatic embryos (FIG. 2).

In a separate experiment, Hi-II maize immature embryos were transformed using Agrobacterium containing PHP25271. After selecting stable, bialaphos-resistant callus events, callus samples from 10 transgenic events were placed on various concentrations of tetracycline (TC). RNA was isolated from callus samples using the PURESCRIPT® RNA isolation kit (Gentra Systems, Inc., Minneapolis, Minn., USA). rtPCR was performed using a Qiagen OneStep RT-PCR kit (Qiagen, Inc., Valencia, Calif., USA), using forward primer PHN107613 to Ω 5' UTR (SEQ ID NO:8):

```
5'TACAACAATTACCAACAACAACAAACAACAAAC 3' and reverse primer PHN107611 to ODP2
(SEQ ID NO: 9):
5'AGAAGGAGATGCCGCCGAGGA 3'
```

PCR conditions for each 20 µl reaction were: denaturation at 94° C. (40 sec/cycle), annealing at 62° C. (1 min/cycle), extension at 72° C. (1 min/cycle), for 34 cycles, and final extension at 72° C. for 15 minutes. This reaction produces an expected product which is 316 bp in length. Results are summarized for calli placed on varying concentrations of TC for two days (Table 9a) and for calli placed on TC for 2 days, followed by an additional 5 days of culture without TC (Table 9b).

As shown in Table 9a, eight out of 10 callus lines produced no rtPCR signal after two days on culture medium alone (no TC), while two produced a weak band. For TC concentrations between 0.25 and 20 mg/L, the majority of callus events produced strong signals, indicating that expression of the ODP2 gene had been induced. Two events, C5 and C10, showed little or no ODP2 expression at any TC concentration. After 5 additional days in culture without TC (Table 9b), the rtPCR signals for many samples were reduced in strength or were absent, indicating decay of TC-induced ODP2 expression after removal of the ligand.

TABLE 9a

| Tet mg/L | \multicolumn{10}{c}{Callus Event} |
|---|---|---|---|---|---|---|---|---|---|---|
| | C1 | C2 | C3 | C4 | C5 | C6 | C7 | C8 | C9 | C10 |
| 0 | | ~ | ~ | | | | | | | |
| 0.25 | + | ~ | + | + | | + | + | + | + | ~ |
| 0.5 | + | + | + | + | | + | | + | + | |
| 1.0 | + | | + | + | | ~ | | + | + | |
| 2.0 | + | + | + | | | + | + | + | + | |
| 5.0 | ~ | | + | + | | + | + | | + | |
| 10.0 | + | | ~ | + | | + | + | + | + | |
| 20.0 | + | + | + | + | | + | + | + | + | |

Blank = no observable band; "~" indicates a weak band; and "+" indicates a strong band.

TABLE 9b

| Tet mg/L | \multicolumn{10}{c}{Callus Event} |
|---|---|---|---|---|---|---|---|---|---|---|
| | C1 | C2 | C3 | C4 | C5 | C6 | C7 | C8 | C9 | C10 |
| 0 | | | | | | | | | | |
| 0.25 | + | | + | | | | | | | |
| 0.5 | | | + | | | | | | | |
| 1.0 | + | | | + | | + | | + | | |
| 2.0 | | | | + | | | + | + | + | |

TABLE 9b-continued

| Tet mg/L | \multicolumn{10}{c}{Callus Event} |
|---|---|---|---|---|---|---|---|---|---|---|
| | C1 | C2 | C3 | C4 | C5 | C6 | C7 | C8 | C9 | C10 |
| 5.0 | + | | + | + | | + | | | ~ | |
| 10.0 | + | | + | + | | + | | + | + | |
| 20.0 | + | ~ | + | + | | + | + | + | | |

Blank = no observable band; "~" indicates a weak band; and "+" indicates a strong band.

The articles "a" and "an" refer to one or more than one of the grammatical object of the article. By way of example, "an element" means one or more of the elements.

All book, journal, patent publications and grants mentioned in the specification are indicative of the level of those skilled in the art. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, certain changes and modifications may be practiced within the scope of the appended claims. These examples and descriptions are illustrative and are not read as limiting the scope of the appended claims.

What is claimed is:

1. An isolated polynucleotide encoding a tetracycline repressor (TetR) polypeptide that binds to a tetracycline operator (TetOp) in the absence of tetracycline or tetracycline analog, wherein the polynucleotide comprises a nucleic acid molecule modified by codon substitution of SEQ ID NO: 1, wherein codons having a higher frequency of usage in a plant are substituted for codons having a lower frequency of usage in a plant, wherein % GC content of the nucleic acid molecule has been increased to at least 50%, and wherein the isolated polynucleotide encodes a TetR polypeptide having at least 95% sequence identity to SEQ ID NO: 2, wherein the % sequence identity is based on the entire coding region and is calculated by the GAP algorithm under default parameters, the nucleic acid molecule having at least 97% sequence identity to SEQ ID NO: 3, 5, 11 or 13.

2. The isolated polynucleotide of claim 1, wherein the isolated polynucleotide has less than 88% sequence identity to SEQ ID NO: 1, wherein the % sequence identity is based on the entire coding region and is calculated by the GAP algorithm under default parameters, and wherein the isolated polynucleotide encodes a TetR polypeptide.

3. The isolated polynucleotide of claim 1, wherein the nucleic acid molecule is SEQ ID NO: 3, 5, 11 or 13.

4. The isolated polynucleotide of claim 1, wherein codon usage frequency in a plant is based on codon frequency usage in a monocot plant or codon frequency usage in a dicot plant.

5. The isolated polynucleotide of claim 4, wherein the plant is selected from the group consisting of corn, rice, wheat, barley, millet, rye, sorghum, oat, soybean, sunflower, safflower, tobacco, cotton, *Arabidopsis*, alfalfa and *Brassica*.

6. The isolated polynucleotide of claim 1, further comprising an operably linked promoter functional in a host cell.

7. A host cell comprising the polynucleotide of claim 1.

8. The host cell of claim 7, wherein the host cell is a plant cell.

9. The host cell of claim 8, wherein the plant cell is from a monocot or a dicot.

10. The host cell of claim 9, wherein the plant cell is selected from the group consisting of rice, wheat, barley, millet, rye, oat, soybean, sunflower, safflower, tobacco, cotton, *Arabidopsis*, alfalfa and *Brassica*.

11. A plant comprising the polynucleotide of claim 1.

12. The plant of claim 11, wherein the plant is a monocot or a dicot.

13. The plant of claim 12, wherein the plant is selected from the group consisting of rice, wheat, barley, millet, rye, sorghum, oat, soybean, sunflower, safflower, tobacco, cotton, *Arabidopsis*, alfalfa and *Brassica*.

14. The host cell of claim 9, wherein the plant cell is from corn.

15. The plant of claim 11, wherein the plant is corn.

* * * * *